US012759958B2

(12) United States Patent
Saito et al.

(10) Patent No.: US 12,759,958 B2
(45) Date of Patent: Oct. 13, 2026

(54) METHODS OF PLASTIC RECYCLING USING HIGHLY EFFICIENT ORGANOCATALYSTS

(71) Applicant: UT-Battelle, LLC, Oak Ridge, TN (US)

(72) Inventors: Tomonori Saito, Knoxville, TN (US); Md Arifuzzaman, Knoxville, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 892 days.

(21) Appl. No.: 18/096,849

(22) Filed: Jan. 13, 2023

(65) Prior Publication Data

US 2024/0067594 A1 Feb. 29, 2024

Related U.S. Application Data

(60) Provisional application No. 63/397,919, filed on Aug. 15, 2022.

(51) Int. Cl.
*C07C 37/055* (2006.01)
*B01J 31/02* (2006.01)
(Continued)

(52) U.S. Cl.
CPC ....... *C07C 37/0555* (2013.01); *B01J 31/0251* (2013.01); *B01J 31/04* (2013.01);
(Continued)

(58) Field of Classification Search
None
See application file for complete search history.

(56) References Cited

U.S. PATENT DOCUMENTS 3,690,227 A 9/1972 Welty
5,055,167 A 10/1991 Heidel et al.
(Continued)

FOREIGN PATENT DOCUMENTS

WO 2017/007965 A1 1/2017
WO WO-2022194587 A2 * 9/2022 ............ C07C 67/03

OTHER PUBLICATIONS

Miran ("Physicochemical properties determined by ΔpKa for protic ionic liquids based on an organic super-strong base with various Bronsted acids" Phys. Chem. Chem. Phys. 2012, p. 5178) (Year: 2012).*

(Continued)

*Primary Examiner* — Amy C Bonaparte
(74) *Attorney, Agent, or Firm* — Scully, Scott, Murphy & Presser, P.C.

(57) ABSTRACT

A method of deconstructing polymer waste into at least one useful breakdown product, wherein the polymer waste contains at least one condensation polymer, the method comprising contacting the polymer waste with a catalyst comprising an organic nitrogen-containing base and a carboxylic acid or ester thereof, in the presence of a protic molecule selected from alcohols, diols, polyols, and amines, at an elevated temperature effective for inducing alcoholysis or aminolysis of the condensation polymer, wherein the useful breakdown products comprise monomer species capable of being polymerized, and the organic nitrogen-containing base has the following structure:

(Continued)

(1)

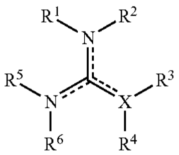

wherein: $R^1$, $R^2$, $R^3$, $R^4$, $R^5$, and $R^6$ are independently selected from hydrogen atom, electron pair, and alkyl groups containing one to three carbon atoms, and wherein any adjacent two of $R^1$, $R^2$, $R^3$, $R^4$, $R^5$, and $R^6$ may optionally interconnect to form a five, six, or seven-membered ring.

13 Claims, 9 Drawing Sheets
(9 of 9 Drawing Sheet(s) Filed in Color)

(51) Int. Cl.
*B01J 31/04* (2006.01)
*C07C 29/09* (2006.01)
*C07C 51/09* (2006.01)
*C08J 11/24* (2006.01)
*C08J 11/28* (2006.01)

(52) U.S. Cl.
CPC ............ *C07C 29/095* (2013.01); *C07C 51/09* (2013.01); *C08J 11/24* (2013.01); *C08J 11/28* (2013.01); *C08J 2367/02* (2013.01)

(56) References Cited

U.S. PATENT DOCUMENTS

| | | | | |
|---|---|---|---|---|
| 6,465,702 | B1 | 10/2002 | Braun et al. | |
| 8,541,477 | B2 | 9/2013 | Alsewailem et al. | |
| 9,914,816 | B2 | 3/2018 | Breyta et al. | |
| 2012/0223270 | A1* | 9/2012 | Alabdulrahman | C07C 67/03 560/64 |
| 2014/0288324 | A1 | 9/2014 | Kraus | |

OTHER PUBLICATIONS

Allen, R.D., et al., "Chemical Recycling of PET. In Circular Economy of Polymers: Topics in Recycling Technologies", American Chemical Society: 2021; vol. 1391, pp. 61-80.
Barboza, L.G.A., et al., "Marine microplastic debris: An emerging issue for food security, food safety and human health", Marine pollution bulletin 2018, 133, 336-348.
Chu, M., et al., "Rational Design of Chemical Catalysis for Plastic Recycling", ACS Catalysis 2022, 12 (8), 4659-4679.
Conti, G.O., et al., "Micro-and nano-plastics in edible fruit and vegetables. The first diet risks assessment for the general population", Environmental Research 2020, 187, 109677.
Cox, K.D., et al., "Human consumption of microplastics", Environmental science & technology 2019, 53 (12), 7068-7074.
Demarteau, J., et al., "Aminolytic upcycling of poly (ethylene terephthalate) wastes using a thermally-stable organocatalyst", Polymer Chemistry 2020, 11 (30), 4875-4882.
Ellis, L.D., et al., "Chemical and biological catalysis for plastics recycling and upcycling", Nature Catalysis 2021, 4 (7), 539-556.
Garcia, J.M., et al., "The future of plastics recycling", Science 2017, 358 (6365), 870-872.
Gausas, L., et al., "Evaluation of Manganese Catalysts for the Hydrogenative Deconstruction of Commercial and End-of-Life Polyurethane Samples", ChemSusChem 2022, 15 (1), e202101705.
Geyer, R., et al., "Production, use, and fate of all plastics ever made", Science Advances 2017, 3 (7), e1700782.
Gibb, B.C., "Plastics are forever", Nature Publishing Group, 2019.
Heiran, R., et al., "Glycolysis: An efficient route for recycling of end of life polyurethane foams", Journal of Polymer Research 2021, 28 (1), 1-19.
Hernandez, L.M., et al., "Plastic teabags release billions of microparticles and nanoparticles into tea", Environmental science & technology 2019, 53 (21), 12300-12310.
Jehanno, C., et al., "Organocatalysis for depolymerisation", Polymer Chemistry 2019, 10 (2), 172-186.
Jehanno, C., et al., "Organocatalysed depolymerisation of PET in a fully sustainable cycle using thermally stable protic ionic salt", Green Chemistry 2018, 20 (6), 1205-1212.
Jehanno, C., et al., "Selective Chemical Upcycling of Mixed Plastics Guided by a Thermally Stable Organocatalyst", Angewandte Chemie International Edition 2021, 60 (12), 6710-6717.
Kumar, A., et al., "Hydrogenative depolymerization of nylons", Journal of the American Chemical Society 2020, 142 (33), 14267-14275.
Lau, W.W.Y., et al., "Evaluating scenarios toward zero plastic pollution", Science 2020, 369 (6510), 1455-1461.
MacLeod, M., et al., "The global threat from plastic pollution", Science 2021, 373 (6550), 61-65.
Mangold, H., et al., "The Frontier of Plastics Recycling: Rethinking Waste as a Resource for High-Value Applications", Macromolecular Chemistry and Physics n/a (n/a), 2100488, 2022.
Nicholson, S.R., et al., "The Critical Role of Process Analysis in Chemical Recycling and Upcycling of Waste Plastics", Annual Review of Chemical and Biomolecular Engineering 2022, 13 (1), null.
Ragusa, A., et al., "Plasticenta: First evidence of microplastics in human placenta", Environment International 2021, 146, 106274.
Roy, P.S., et al., "Strategic approach towards plastic waste valorization: challenges and promising chemical upcycling possibilities", ChemSusChem 2021, 14 (19), 4007-4027.
Vollmer, I., et al., "Beyond Mechanical Recycling: Giving New Life to Plastic Waste", Angewandte Chemie International Edition 2020, 59 (36), 15402-15423.
Worch, J.C., et al., "100th anniversary of macromolecular science viewpoint: Toward catalytic chemical recycling of waste (and future) plastics", ACS Macro Letters 2020, 9 (11), 1494-1506.
Zhang, F., et al., "Polyethylene upcycling to long-chain alkylaromatics by tandem hydrogenolysis/aromatization", Science 2020, 370 (6515), 437-441.
Zhao, Y., et al., "A new local density functional for main-group thermochemistry, transition metal bonding, thermochemical kinetics, and noncovalent interactions", The Journal of chemical physics 2006, 125 (19), 194101.
Zheng, J., et al., "Strategies to reduce the global carbon footprint of plastics", Nature Climate Change 2019, 9 (5), 374-378.
International Search Report and Written Opinion dated Jun. 16, 2023 issued in PCT/US 23/10769, 11 pages.
Pubmed Compound Record for CID 17889673, 'Ethene-1,1-diamine', U.S. National Library of Medicine, https://pubchem.ncbl.nlm.nih.gov/compound/17889673, Dec. 4, 2007, 12 pages.

* cited by examiner

Kinetic Study

2G

2H

METHODS OF PLASTIC RECYCLING USING HIGHLY EFFICIENT ORGANOCATALYSTS

CROSS REFERENCE TO RELATED APPLICATION

The present application claims benefit of U.S. Provisional Application No. 63/397,919, filed on Aug. 15, 2022, all of the contents of which are incorporated herein by reference.

STATEMENT REGARDING FEDERALLY SPONSORED RESEARCH

This invention was made with government support under Prime Contract Nos. DE-AC05-000R22725 and AC02-07CH11358 awarded by the U.S. Department of Energy. The government has certain rights in the invention.

FIELD OF THE DISCLOSURE

The present disclosure generally relates to methods of breaking down and recycling plastic waste. The present disclosure more particularly relates to methods of deconstructing polymer waste into monomeric or other useful molecular products by use of a catalyst.

BACKGROUND

Plastics have transformed everyday life because of their robust mechanical properties, lightweight, scalability, versatility, and functional performance. 10.5 billion metric tons of plastics have been produced worldwide, and the annual production rate approaches more than 380 million metric tons (Mt) (M. Chu et al., *ACS Catalysis,* 2022, 12 (18), 4659-4679). Due to inadequate recycling and upcycling paths, plastics-derived waste poses a global challenge for end-of-life management. Nearly 79% of produced plastics are estimated to enter landfills or accumulate in the natural environment, and 12% are incinerated (R. Geyer et al., *Science Advances* 2017, 3 (7), e1700782). Only about 9% of plastic waste has been recycled typically by mechanical recycling, and most recycled plastics are currently downcycled toward less recyclable and lower-value products (B. C. Gibb, *Nat. Chem.* 2019, 11 (5), 394-395). Commodity plastics used yearly in the USA alone account for an estimated 3.2 quadrillion BTUs (quads) of energy and 104 Mt $CO_2$ equivalent of greenhouse gas (GHG) emissions (S. R. Nicholson et al., *Joule* 2021, 5 (3), 673-686).

One of the most effective strategies to mitigate GHG emissions includes establishing closed-loop circularity of plastic, such as chemical recycling, to exchange the fossil carbon feedstock and minimize the energy and carbon inputs in the entire plastics supply chain (R. Meys et al., *Science* 2021, 374 (6563), 71-76). Significant scientific advancement is needed to achieve the closed-loop circularity of plastics by replacing fossil-based carbon feedstocks with bio-based or waste-sourced feedstocks from the chemical recycling of discarded plastics to a much greater extent. Establishing circular plastic recycling on a global scale is estimated to alleviate energy consumption equivalent to 3.5 billion barrels of oil, valued at approximately $176 billion, annually (M. Hong et al., *Green Chemistry* 2017, 19 (16), 3692-3706).

Among various commodity plastics, condensation polymers such as poly(ethylene terephthalate) (PET), poly(carbonate) (PC), poly(urethane) (PU), and poly(amide) (PA) comprise about 30% of global plastic production, with PETs and PUs being the 5th and 6th most-produced plastics, respectively (J. C. Worch et al., *ACS Macro Letters* 2020, 9 (11), 1494-1506). The chemical recycling of condensation polymers by such methods as glycolysis is an evolving versatile route for creating value-added materials from plastic waste or regenerating essential monomers for use in a plastic circularity. Several innovative solutions, such as metal-based catalysts, ionic liquids, or deep-eutectic solvents have been recently reported to achieve depolymerization of individual polar plastics (PET, PC, PU, and PA) into monomer products (FIG. 1)(G. W. Coates et al., *Nature Reviews Materials* 2020, 5 (7), 501-516). Despite these advancements, many challenges remain, including the possible presence of metal in the final product, limited monomer yields, requirement of a specific catalyst for each polymer, laborious sorting procedures, and purification procedures that entail high environmental and economic costs.

Organocatalysts provide many advantages for deconstructing condensation polymers. Their greener characters of good selectivity, thermal stability, non-volatility, and low flammability make them good substitutes for traditional heterogeneous catalysts (C. Jehanno et al., *Green Chemistry* 2018, 20 (6), 1205-1212). Protic ionic salt (PIS) based organocatalysts have been used for the deconstruction of condensation polymers. The catalytic activity of PIS is governed by a dual-activation mechanism, where the anion activates the nucleophile and the cation activates the electrophile (C=O bond) (C. Jehanno et al., *Angewandte Chemie International Edition* 2021, 60 (12), 6710-6717). One such PIS catalyst, triazabicyclododecane:methanesulfonic acid (TBD:MSA), has shown promise for the deconstruction of PC and PET individually and their mixture (C. Jehanno et al., *Green Chemistry* 2018, 20 (6), 1205-1212). The development of TBD:MSA has shed light on the design of PIS organocatalysts, but a significant challenge remains for achieving deconstruction in a wide variety of condensation polymers and their mixtures, as well as various other mixed plastics (J. C. Worch et al., *ACS Macro Letters* 2020, 9 (11), 1494-1506).

Currently, mixed plastics are difficult to recycle from post-consumer waste because of the need for sorting and separation before reprocessing. From a raw cost perspective, manufacturing new plastic products from virgin feedstocks is typically more cost-efficient than sorting and reusing reprocessed material. The low recycling rate is exacerbated by increased mixed-waste streams of multicomponent plastics, such as composites and packaging. No single catalyst or technology is currently available for converting a mixture of plastics in one pot and selectively into valuable chemicals. There would be a significant benefit in a method that can efficiently deconstruct mixed plastic waste, with the capability of deconstructing the different polymers in the mixture simultaneously or sequentially.

SUMMARY OF THE DISCLOSURE

In a first aspect, the present disclosure is directed to highly efficient PIS organocatalysts that can efficiently deconstruct mixed waste of PC, PU, PET, and PA in a single batch via selective cleavage of amide, carbonate, urethane, and ester bonds. The designed organocatalyst can deconstruct condensation polymers selectively, while keeping other polymers, such as polyolefins (e.g., poly(ethylene) (PE) and poly(propylene) (PP)) or cotton, intact to permit their facile separation from the mixture. The chemical deconstruction process described herein can advantageously be applied to a substantial portion of existing mixed plastics and provide a way toward achieving closed-loop circularity of plastics and carbon neutrality.

The catalyst includes an organic nitrogen-containing base and a carboxylic acid or ester thereof, wherein the organic nitrogen-containing base and carboxylic acid or ester are typically complexed with each other. Notably, although a carboxylic ester may be used, the carboxylic ester is typically converted to the corresponding carboxylic acid during the deconstruction process.

The organic nitrogen-containing base (i.e., "base") may be more specifically depicted by the following formula:

(1)

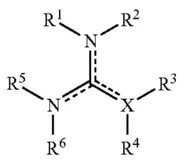

wherein $R^1$, $R^2$, $R^3$, $R^4$, $R^5$, and $R^6$ are independently selected from hydrogen atom, electron pair, and alkyl groups containing one to three carbon atoms, wherein: $R^1$ and $R^2$ may optionally interconnect to form a five, six, or seven-membered ring; $R^2$ and $R^3$ may optionally interconnect to form a five, six, or seven-membered ring; $R^3$ and $R^4$ may optionally interconnect to form a five, six, or seven-membered ring; $R^4$ and $R^6$ may optionally interconnect to form a five, six, or seven-membered ring; $R^5$ and $R^6$ may optionally interconnect to form a five, six, or seven-membered ring; and $R^1$ and $R^5$ may optionally interconnect to form a five, six, or seven-membered ring; X is C or N; and the dotted lines represent optional double bonds. In specific embodiments, the base may have any of the structures shown in Formulas (1a), (1b), (1c), (1d), (1e), (1f), (1g), (1h), and (1i).

The catalyst includes or exclusively contains any of the above bases combined with a carboxylic acid or ester thereof, wherein the carboxylic acid or ester thereof may have the following structure:

(2)

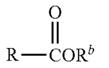

wherein R is a hydrogen atom or a hydrocarbon group containing 1-12 carbon atoms, with optional substitution with one or more fluorine atoms and/or $OR^b$ groups and optional substitution with another carboxylic acid group or ester thereof; and $R^b$ is selected from hydrogen atom and alkyl groups containing one to three carbon atoms. In some embodiments, R is a hydrocarbon group containing 1-6, 1-5, 1-4, 1-3, or 1-2 carbon atoms, with optional substitution with one or more halogen (e.g., fluorine, chlorine, bromine, and/or iodine) atoms. In some embodiments, the carboxylic acid or ester thereof is trifluoroacetic acid or an ester thereof.

Any one or more of the above types of carboxylic acid or ester species may be combined with any one or more bases of the Formulas (1), (1a), (1b), (1c), (1d), (1e), (1f), (1g), (1h), and (1i), as further described below, to result in the catalyst. The carboxylic acid or ester (A) species may be combined with the base (B) species in any desired B:A molar ratio, such as a B:A molar ratio within a range of 0.05:1 to 1:0.05, a B:A molar ratio within a range of 0.2:1 to 1:0.2, a B:A molar ratio within a range of 0.5:1 to 1:0.5, or a B:A molar ratio of about 1:1.

In another aspect, the present disclosure is directed to a method of deconstructing polymer waste into at least one useful breakdown product, wherein the polymer waste contains at least one condensation polymer. The method includes contacting the polymer waste with any of the catalysts described above in the presence of a protic molecule selected from alcohols, diols, polyols, and amines, at an elevated temperature effective for inducing alcoholysis or aminolysis of the condensation polymer, wherein the useful breakdown products comprise monomer species capable of being polymerized. In some embodiments, the protic molecule is a diol, such as ethylene glycol. In some embodiments, the condensation polymer is selected from at least one of the group consisting of a polyester, polyurethane, polycarbonate, and polyamide. In some embodiments, the condensation polymer waste contains at least two different types of condensation polymers. In some embodiments, the condensation polymer waste contains a polyester, such as polyethylene terephthalate, wherein at least one useful breakdown product may be bis(2-hydroxyethyl) terephthalate. An exemplary schematic of the process is shown in FIG. 1B.

BRIEF DESCRIPTION OF THE FIGURES

The patent or application file contains at least three drawings executed in color. Copies of this patent or patent application publication with color drawing(s) will be provided by the Office upon request and payment of the necessary fee.

FIG. 2A shows formation of TBD:TFA. The $^1H$ NMR spectrum (FIG. 2B) shows the disappearance of a peak at δ13.84 ppm (•) for TFA (FIG. 2B, top) and shifting of the peak from δ4.14 ppm (•) (FIG. 2B, bottom) for TBD to δ8.12 ppm (•), indicating the formation of the TBD:TFA (FIG. 2B, middle). FIG. 2C shows deconstruction of PET by using TBD:TFA to yield a pure BHET crystal through recrystallization in water. The $^1H$ NMR spectrum before (FIG. 2D, bottom) and after (FIG. 2D, top) purification show pure BHET, and the successful removal of the catalyst and excess EG. FIG. 2E is a graph showing catalytic activity of TBD:TFA (gold), which shows complete conversion at 2 h compared to TBD:MSA (purple), TBD (gray), TBD:mTFA (brown), and mTBD:TFA (orange). FIG. 2F is a graph showing recyclability of the catalyst among PC, PU, PET, and PA deconstruction. FIGS. 2G and 2H show results and conditions, respectively, of a kinetic study of PC, PU, PET, and PA to yield corresponding monomer BPA (black), MDA (red), BHET (blue), and CPL (green), respectively. Reaction condition: Polymer (1 eq.), EG (10 eq.), Cat. (0.05 eq.) at 180° C. (110-210° C. for H) for 2 h.

FIG. 4A shows sequential deconstruction of mixed PC, PU, PET, and PA using TBD:TFA (0.05 eq.) and EG (10 eq.) for 2 h where white circle symbolizes PC, red triangle symbolizes PU, blue diamond symbolizes PET and green square symbolizes PA. At 130° C. (I), PC fully converts to BPA while PU, PET, and PA are kept intact (B & B'). At 160° C. (II), PU fully converts to MDA with small conversion of PET while PA is kept intact (C & C'). At 180° C. (III), PET fully converts to BHET while keeping PA unreacted (D & D'). Finally, at 210° C. (IV), the remaining unreacted PA fully converts to CPL (E & E'). Alternatively, directly heating at 210° C. (V) can deconstruct PC, PU, PET, and PA once to yield the mixture of corresponding BPA, MDA, BHET, and CPL. FIG. 4B (top row) shows deconstruction of the PET bottle and PP cap mixture to produce BHET while keeping PP intact. FIG. 4B (middle row) shows that the combination of PC, PU, PET, and PA consumer products with a piece of PE bag is deconstructed to produce corresponding monomer BPA, MDA, BHET, and CPL, respectively, while keeping PE intact. FIG. 4B (bottom row) shows the deconstruction of fabric based on polyester (40%) and cotton (60%) to produce BHET monomer, while unreacted cotton can be readily separated. Energy footprint (FIG. 4C) and carbon footprint (FIG. 4D) of PC, PU, PET, and PA production by conventional petroleum-based approach against the reconstruction of PC, PU, PET, and PA using the deconstructed monomer by TBD:TFA-based process.

DETAILED DESCRIPTION

Figure 1:
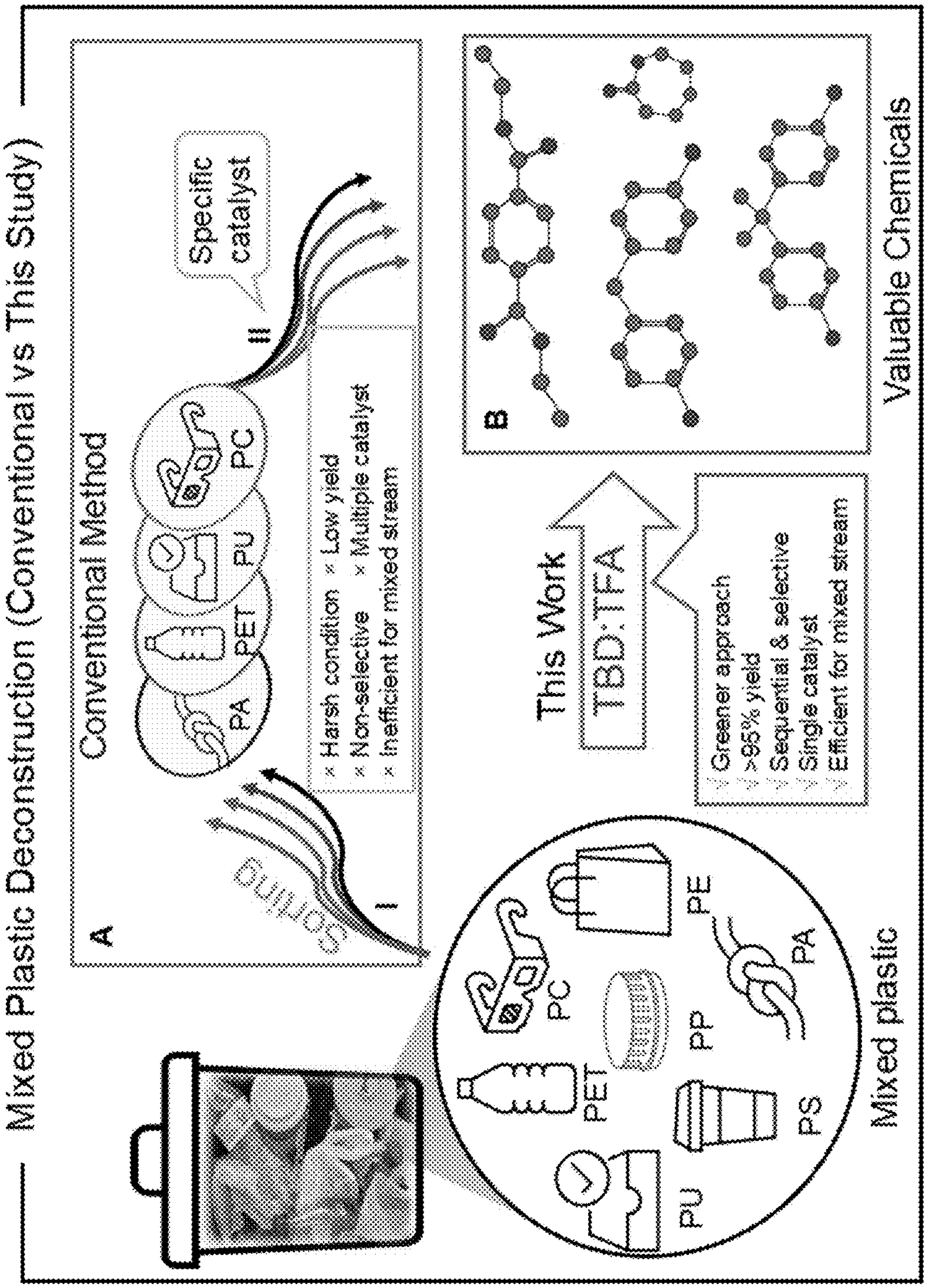
FIG. 1 (portions A and B). Methods of mixed plastic deconstruction. Portion A schematically depicts conventional methods for breaking down plastics, wherein the methods include sorting of individual polymers, followed by mechanical recycling or chemical recycling with a specific catalyst. Portion B shows possible valuable products produced by the presently disclosed method, which provides efficient deconstruction of mixed plastic (PC, PU, PET, and PA) by a tailored organocatalyst to produce valuable chemicals.

In a first aspect, the present disclosure is directed to a catalyst containing an organic nitrogen-containing base (i.e., "base" or "B species") and a carboxylic acid or ester thereof (i.e., "acid" or "A species"). The base is typically complexed with the acid in the catalyst. The carboxylic acid or ester (A) species may be combined with the base (B) species in any desired B:A molar ratio, wherein the B:A molar ratio may have a B molar value and A molar value independently selected from, for example, 0.05, 0.06, 0.07, 0.08, 0.09, 0.1, 0.2, 0.25, 0.3, 0.4, 0.5, 0.6, 0.7, 0.8, 0.9, and 1. The B:A molar ratio may also be within a range of B:A molar ratios. In some embodiments, the B:A molar ratio is within a range of 0.05:1 to 1:0.05 (1:20 to 20:1). In other embodiments, the B:A molar ratio is within a range of 0.2:1 to 1:0.2 (or 1:5 to 5:1). In other embodiments, the B:A molar ratio is within a range of 0.5:1 to 1:0.5 (or 1:2 to 2:1). In other embodiments, the B:A molar ratio is about 1:1.

In embodiments, the organic nitrogen-containing base has the following structure:

(1)

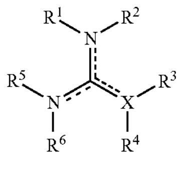

In Formula (1), the variables $R^1$, $R^2$, $R^3$, $R^4$, $R^5$, and $R^6$ are independently selected from hydrogen atom, electron pair, and alkyl groups containing one to three carbon atoms. Examples of alkyl groups containing one to three carbon atoms include methyl, ethyl, n-propyl, and isopropyl. The dotted lines represent optional double bonds. If a nitrogen atom in Formula (1) or sub-formula thereof is engaged in a carbon-nitrogen double bond, a substituent shown attached to the nitrogen atom is an electron pair to maintain charge neutrality. The variable X is C, $CR^a$, or N, wherein $R^a$ is selected from hydrogen atom and alkyl groups containing one to three carbon atoms. Notably, by the rules of chemistry, the variable $R^1$, $R^2$, $R^3$, $R^4$, $R^5$, or $R^6$ can only be an electron pair when the electron pair is attached to a nitrogen atom engaged in a carbon-nitrogen double bond. Similarly, by the rules of chemistry, X is C only when C is engaged in a carbon-carbon double bond, and X is $CR^a$ only when the carbon atom in $CR^a$ is engaged exclusively in carbon-carbon single bonds. In some embodiments, all of $R^1$, $R^2$, $R^3$, $R^4$, $R^5$, and $R^6$ are hydrogen atoms. In other embodiments, one, two, three, four, five, or all of $R^1$, $R^2$, $R^3$, $R^4$, $R^5$, and $R^6$ are alkyl groups containing one to three carbon atoms, or more particularly, one, two, three, four, five, or all of $R^1$, $R^2$, $R^3$, $R^4$, $R^5$, and $R^6$ are selected from methyl groups, ethyl groups, n-propyl groups, or isopropyl groups or selected from a combination thereof.

In a first set of embodiments, $R^1$ and $R^2$ optionally interconnect to form a five, six, or seven-membered ring. In some embodiments, $R^1$ and $R^2$ interconnect to form a five, six, or seven-membered ring, while in other embodiments, $R^1$ and $R^2$ do not interconnect.

In a second set of embodiments, $R^2$ and $R^3$ optionally interconnect to form a five, six, or seven-membered ring. In some embodiments, $R^2$ and $R^3$ interconnect to form a five, six, or seven-membered ring, while in other embodiments, $R^2$ and $R^3$ do not interconnect.

In a third set of embodiments, $R^3$ and $R^4$ optionally interconnect to form a five, six, or seven-membered ring. In some embodiments, $R^3$ and $R^4$ interconnect to form a five, six, or seven-membered ring, while in other embodiments, $R^3$ and $R^4$ do not interconnect.

In a fourth set of embodiments, $R^4$ and $R^6$ optionally interconnect to form a five, six, or seven-membered ring. In some embodiments, $R^4$ and $R^6$ interconnect to form a five, six, or seven-membered ring, while in other embodiments, $R^4$ and $R^6$ do not interconnect.

In a fourth set of embodiments, $R^5$ and $R^6$ optionally interconnect to form a five, six, or seven-membered ring. In some embodiments, $R^5$ and $R^6$ interconnect to form a five, six, or seven-membered ring, while in other embodiments, $R^5$ and $R^6$ do not interconnect.

In a fifth set of embodiments, $R^1$ and $R^5$ optionally interconnect to form a five, six, or seven-membered ring. In some embodiments, $R^1$ and $R^5$ interconnect to form a five, six, or seven-membered ring, while in other embodiments, $R^1$ and $R^5$ do not interconnect.

Any two of the above first to fifth embodiments may be combined to result in a bicyclic compound within the scope of Formula (1). Any three of the above first to fifth embodiments may be combined to result in a tricyclic compound within the scope of Formula (1).

In some embodiments of Formula (1), the organic nitrogen-containing base has the following structure:

(1a)

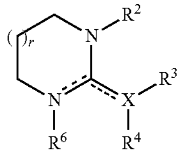

In Formula (1a), $R^2$, $R^3$, $R^4$, $R^6$ and X are as defined earlier above, and the variable r is a value of 0, 1, or 2. When r is 0, a five-membered ring results. When r is 1, a six-membered ring results. When r is 2, a seven-membered ring results. In some embodiments of Formula (1a), X is C or $CR^a$. In other embodiments of Formula (1a), X is N. In some embodiments, all of $R^2$, $R^3$, $R^4$, $R^6$ are hydrogen atoms. In other embodiments, one, two, three, or all of $R^2$, $R^3$, $R^4$, $R^6$ are alkyl groups containing one to three carbon atoms, or more particularly, one, two, three, or all of $R^2$, $R^3$, $R^4$, $R^6$ are selected from methyl groups, ethyl groups, n-propyl groups, or isopropyl groups or selected from a combination thereof. In the case where a nitrogen atom in Formula (1a) is attached to a hydrogen atom or alkyl group, the nitrogen atom is not engaged in a double bond since the presence of a double bond in such circumstance would result in a positively charged molecule, but molecules of Formula (1) and sub-formulas thereof are uncharged (neutral) for purposes of the present disclosure. If a nitrogen atom in Formula (1) or sub-formula thereof is engaged in a carbon-nitrogen double bond, the substituent (e.g., $R^4$ or $R^6$) is an electron pair in that case to maintain charge neutrality (no charge). In some embodiments, $R^6$ is an electron pair and the nitrogen atom attached to $R^6$ is engaged in a carbon-nitrogen double bond, in which case the remaining optional double bond shown in Formula (1a) is not present. In further or alternative embodiments, $R^4$ is an alkyl group, such as any of the alkyl groups provided above, particularly methyl or ethyl. In further or alternative embodiments, $R^2$ and $R^3$ optionally interconnect to form a five, six, or seven-membered ring. In further or alternative embodiments, $R^3$ and $R^4$ optionally interconnect to form a five, six, or seven-membered ring. In further or alternative embodiments, $R^4$ and $R^6$ optionally interconnect to form a five, six, or seven-membered ring.

In some embodiments of Formula (1a), the organic nitrogen-containing base has the following structure:

(1b)

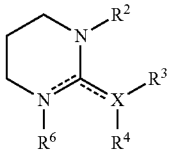

In Formula (1b), $R^2$, $R^3$, $R^4$, $R^6$ and X are as defined earlier above. In some embodiments of Formula (1b), X is C or $CR^a$. In other embodiments of Formula (1b), X is N. In some embodiments, all of $R^2$, $R^3$, $R^4$, $R^6$ are hydrogen atoms. In other embodiments, one, two, three, or all of $R^2$, $R^3$, $R^4$, $R^6$ are alkyl groups containing one to three carbon atoms, or more particularly, one, two, three, or all of $R^2$, $R^3$, $R^4$, $R^6$ are selected from methyl groups, ethyl groups, n-propyl groups, or isopropyl groups or selected from a combination thereof. In some embodiments, $R^6$ is an electron pair and the nitrogen atom attached to $R^6$ is engaged in a carbon-nitrogen double bond, in which case the remaining optional double bond shown in Formula (1a) is not present. In further or alternative embodiments, $R^4$ is an alkyl group, such as any of the alkyl groups provided above, particularly methyl or ethyl. In further or alternative embodiments, $R^2$ and $R^3$ optionally interconnect to form a five, six, or seven-membered ring. In further or alternative embodiments, $R^3$ and $R^4$ optionally interconnect to form a five, six, or seven-membered ring. In further or alternative embodiments, $R^4$ and $R^6$ optionally interconnect to form a five, six, or seven-membered ring.

In some embodiments of Formula (1), the organic nitrogen-containing base has the following structure:

(1c)

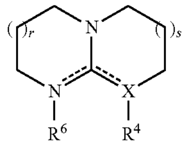

In Formula (1c), $R^4$, $R^6$ and X are as defined earlier above, and the variables r and s are each independently a value of 0, 1, or 2. When r or s is 0, a five-membered ring results. When r or s is 1, a six-membered ring results. When r or s is 2, a seven-membered ring results. In different embodiments, r and s are both 0; or r and s are both 1; or r and s are both 2; or r is 0 and s is 1; or r is 0 and s is 2; or r is 1 and s is 0; or r is 1 and s is 2; or r is 2 and s is 0; or r is 2 and s is 1. In some embodiments of Formula (1c), X is C or $CR^a$. In other embodiments of Formula (1c), X is N. In some embodiments, $R^4$ and $R^6$ are hydrogen atoms. In other embodiments, one or both of $R^4$ and $R^6$ are alkyl groups containing one to three carbon atoms, or more particularly, one or both of $R^4$ and $R^6$ are selected from methyl groups, ethyl groups, n-propyl groups, or isopropyl groups or selected from a combination thereof. In some embodiments, $R^6$ is an electron pair and the nitrogen atom attached to $R^6$ is engaged in a carbon-nitrogen double bond, in which case the remaining optional double bond shown in Formula (1c) is not present. In further or alternative embodiments, $R^4$ is an alkyl group, such as any of the alkyl groups provided above, particularly methyl or ethyl. In further or alternative embodiments, $R^4$ and $R^6$ optionally interconnect to form a five, six, or seven-membered ring.

In some embodiments of Formula (1c), the organic nitrogen-containing base has the following structure:

(1d)

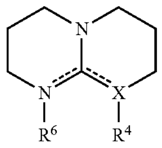

In Formula (1d), $R^4$, $R^6$ and X are as defined earlier above. In some embodiments of Formula (1d), X is C or $CR^a$. In other embodiments of Formula (1d), X is N. In some embodiments, $R^4$ and $R^6$ are hydrogen atoms. In other embodiments, one or both of $R^4$ and $R^6$ are alkyl groups containing one to three carbon atoms, or more particularly, one or both of $R^4$ and $R^6$ are selected from methyl groups, ethyl groups, n-propyl groups, or isopropyl groups or selected from a combination thereof. In some embodiments, $R^6$ is an electron pair and the nitrogen atom attached to $R^6$ is engaged in a carbon-nitrogen double bond, in which case the remaining optional double bond shown in Formula (1d) is not present. In further or alternative embodiments, $R^4$ is an alkyl group, such as any of the alkyl groups provided above, particularly methyl or ethyl. In further or alternative embodiments, $R^4$ and $R^6$ optionally interconnect to form a five, six, or seven-membered ring.

In some embodiments of Formula (1c), the organic nitrogen-containing base has the following structure:

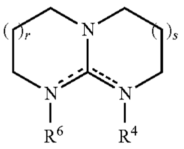

(1e)

In Formula (1e), $R^4$ and $R^6$ are as defined earlier above, and the variables r and s are each independently a value of 0, 1, or 2. When r or s is 0, a five-membered ring results. When r or s is 1, a six-membered ring results. When r or s is 2, a seven-membered ring results. In different embodiments, r and s are both 0; or r and s are both 1; or r and s are both 2; or r is 0 and s is 1; or r is 0 and s is 2; or r is 1 and s is 0; or r is 1 and s is 2; or r is 2 and s is 0; or r is 2 and s is 1. In some embodiments, $R^4$ and $R^6$ are hydrogen atoms. In other embodiments, one or both of $R^4$ and $R^6$ are alkyl groups containing one to three carbon atoms, or more particularly, one or both of $R^4$ and $R^6$ are selected from methyl groups, ethyl groups, n-propyl groups, or isopropyl groups or selected from a combination thereof. In some embodiments, $R^6$ is an electron pair and the nitrogen atom attached to $R^6$ is engaged in a carbon-nitrogen double bond, in which case the remaining optional double bond shown in Formula (1e) is not present. In further or alternative embodiments, $R^4$ is an alkyl group, such as any of the alkyl groups provided above, particularly methyl or ethyl. In further or alternative embodiments, $R^4$ and $R^6$ optionally interconnect to form a five, six, or seven-membered ring.

In some embodiments of Formula (1e), the organic nitrogen-containing base has the following structure:

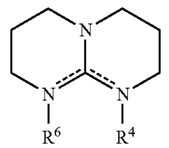

(1f)

In Formula (1f), $R^4$ and $R^6$ are as defined earlier above. In some embodiments, $R^4$ and $R^6$ are hydrogen atoms. In other embodiments, one or both of $R^4$ and $R^6$ are alkyl groups containing one to three carbon atoms, or more particularly, one or both of $R^4$ and $R^6$ are selected from methyl groups, ethyl groups, n-propyl groups, or isopropyl groups or selected from a combination thereof. In some embodiments, $R^6$ is an electron pair and the nitrogen atom attached to $R^6$ is engaged in a carbon-nitrogen double bond, in which case the remaining optional double bond shown in Formula (1f) is not present. In further or alternative embodiments, $R^4$ is an alkyl group, such as any of the alkyl groups provided above, particularly methyl or ethyl. In further or alternative embodiments, $R^4$ and $R^6$ optionally interconnect to form a five, six, or seven-membered ring.

In some embodiments of Formula (1), the organic nitrogen-containing base has the following structure:

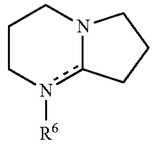

(1g)

In Formula (1g), $R^6$ is as defined earlier above. In some embodiments, $R^6$ is a hydrogen atom. In other embodiments, $R^6$ is an alkyl group containing one to three carbon atoms, or more particularly, $R^6$ is selected from methyl groups, ethyl groups, n-propyl groups, or isopropyl groups or selected from a combination thereof. In the case where $R^6$ is a hydrogen atom or alkyl group, the optional double bond is not present. In some embodiments, $R^6$ is an electron pair and the nitrogen atom attached to $R^6$ is engaged in a carbon-nitrogen double bond.

In some embodiments of Formula (1), the organic nitrogen-containing base has the following structure:

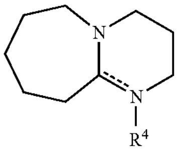

(1h)

In Formula (1h), $R^4$ is as defined earlier above. In some embodiments, $R^4$ is a hydrogen atom. In other embodiments, $R^4$ is an alkyl group containing one to three carbon atoms, or more particularly, $R^4$ is selected from methyl groups, ethyl groups, n-propyl groups, or isopropyl groups or selected from a combination thereof. In the case where $R^4$ is a hydrogen atom or alkyl group, the optional double bond is not present. In some embodiments, $R^4$ is an electron pair and the nitrogen atom attached to $R^4$ is engaged in a carbon-nitrogen double bond.

In some embodiments of Formula (1), the organic nitrogen-containing base has the following structure:

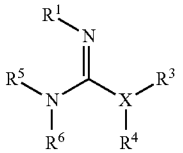

(1i)

In Formula (1i), $R^1$, $R^3$, $R^4$, $R^5$, $R^6$ and X are as defined earlier above, except that $R^1$, $R^3$, $R^4$, $R^5$, and $R^6$ are not permitted to interconnect. In some embodiments of Formula (1i), X is $CR^a$. In other embodiments of Formula (1i), X is N. In some embodiments, all of $R^1$, $R^3$, $R^4$, $R^5$, $R^6$ are hydrogen atoms. In other embodiments, one, two, three, four, or all of $R^1$, $R^3$, $R^4$, $R^5$, $R^6$ are alkyl groups containing one to three carbon atoms, or more particularly, one, two, three, four, or all of $R^1$, $R^3$, $R^4$, $R^5$, $R^6$ are selected from methyl groups, ethyl groups, n-propyl groups, or isopropyl groups or selected from a combination thereof. In some embodiments, $R^1$, $R^3$, and $R^5$ are selected from alkyl groups containing one to three carbon atoms, such as any of the alkyl groups provided above, or $R^1$, $R^3$, and $R^5$ are methyl groups.

Some specific examples of organic nitrogen-containing bases include:

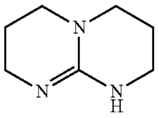

TBD

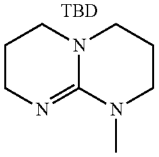

(mTBD)

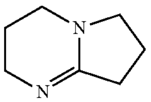

(DBN)

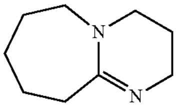

(DBU)

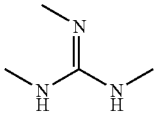

(TMG)

As indicated earlier above, the base, which may have any of the structures within Formulas (1), (1a), (1b), (1c), (1d), (1e), (1f), (1h), (1i), or specific structures provided above, is in combination with (typically, complexed with) a carboxylic acid or ester thereof in the catalyst. The base and acid can be included in the catalyst in any suitable molar ratio, such as any of those provided earlier above.

The carboxylic acid or ester thereof may have the following structure:

(2)

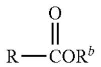

In Formula (2), R is a hydrogen atom (H) or a hydrocarbon group containing 1-12 carbon atoms. In different embodiments, the hydrocarbon group R contains, for example, 1, 2, 3, 4, 5, 6, 7, 8, 9, 10, 11, or 12 carbon atoms, or a number of carbon atoms within a particular range bounded by any two of the foregoing carbon numbers (e.g., 1-12, 1-8, 1-6, 1-5, 1-4, 1-3, 2-12, 2-8, 2-6, 2-5, 2-4, or 2-3 carbon atoms). As used herein, the term “hydrocarbon group” (also denoted by the group R) is defined as a chemical group containing at least carbon and hydrogen atoms. In some embodiments, R is composed solely of carbon and hydrogen. In other embodiments, R is composed of carbon and possibly hydrogen atoms except that the hydrocarbon group may (i.e., optionally) be substituted with one or more halogen (e.g., fluorine, chlorine, bromine, or iodine) atoms to result in partial or complete halogenation of the hydrocarbon group. The group R may or may not be substituted with one or more $OR^b$ groups, wherein $R^b$ is selected from hydrogen atom and alkyl groups containing one to three carbon atoms, as provided earlier above for $R^a$. The group R may or may not be substituted with another (additional) carboxylic acid group or ester thereof to result in a dicarboxylic acid. In different embodiments, the group R may be unsubstituted (i.e., contain only carbon and hydrogen), or may be substituted with one or more halogen atoms, or may be substituted with one or more $OR^b$ groups, or may be substituted with an additional carboxylic acid group, or may be substituted with a combination of halogen and $OR^b$ groups or a combination of halogen and additional carboxylic acid groups or a combination of $OR^b$ and additional carboxylic acid groups.

In a first set of embodiments, the hydrocarbon group (R) is a saturated and straight-chained group, i.e., a straight-chained (linear) alkyl group. Some examples of straight-chained alkyl groups include methyl, ethyl, n-propyl, n-butyl, n-pentyl, n-hexyl, n-heptyl, n-octyl, n-nonyl, n-decyl, n-undecyl, and n-dodecyl groups. Any of the foregoing linear alkyl groups may or may not be substituted with one or more halogen (e.g., fluorine, chlorine, bromine, or iodine) atoms to result in partial or complete halogenation of the linear alkyl group. Any of the foregoing linear alkyl groups may or may not be substituted with one or more OR b groups, or may be substituted with an additional carboxylic acid group, or may be substituted with a combination of halogen and $OR^b$ groups or a combination of halogen and additional carboxylic acid groups or a combination of $OR^b$ and additional carboxylic acid groups.

In a second set of embodiments, the hydrocarbon group (R) is saturated and branched, i.e., a branched alkyl group. Some examples of branched alkyl groups include isopropyl (2-propyl), isobutyl (2-methylprop-1-yl), sec-butyl (2-butyl), t-butyl (1,1-dimethylethyl-1-yl), 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, 1,2,2-trimethylprop-1-yl groups, isoheptyl, isooctyl, and the numerous other branched alkyl groups having up to 12 carbon atoms, wherein the “1-yl” suffix represents the point of attachment of the group. Any of the foregoing branched alkyl groups may or may not be substituted with one or more halogen (e.g., fluorine, chlorine, bromine, or iodine) atoms to result in partial or complete halogenation of the branched alkyl group. Any of the foregoing branched alkyl groups may or may not be substituted with one or more $OR^b$ groups, or may be substituted with an additional carboxylic acid group, or may be substituted with a combination of halogen and $OR^b$ groups or a combination of halogen and additional carboxylic acid groups or a combination of $OR^b$ and additional carboxylic acid groups.

In a third set of embodiments, the hydrocarbon group (R) is saturated and cyclic, i.e., a cycloalkyl group. Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Any of the foregoing cycloalkyl groups may or may not be substituted with one or more halogen (e.g., fluorine, chlorine, bromine, or iodine) atoms to result in partial or complete halogenation of the cycloalkyl group. Any of the foregoing cycloalkyl groups may or may not be substituted with one or more $OR^b$ groups, or may be substituted with an additional carboxylic acid group, or may be substituted with a combination of halogen and $OR^b$ groups or a combination of halogen and additional carboxylic acid groups or a combination of $OR^b$ and additional carboxylic acid groups.

In a fourth set of embodiments, the hydrocarbon group (R) is unsaturated and straight-chained, i.e., a straight-chained (linear) olefinic or alkenyl group. The unsaturation occurs by the presence of one or more carbon-carbon double bonds and/or one or more carbon-carbon triple bonds. Some examples of straight-chained olefinic groups include vinyl, propen-1-yl (allyl), 3-buten-1-yl ($CH_2$═CH—$CH_2$—$CH_2$—), 2-buten-1-yl ($CH_2$—CH═CH—$CH_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), 3-butynyl, and the numerous other straight-chained alkenyl or alkynyl groups having up to 12 carbon atoms. Any of the foregoing linear alkenyl groups may or may not be substituted with one or more halogen (e.g., fluorine, chlorine, bromine, or iodine) atoms to result in partial or complete halogenation of the linear alkenyl group. Any of the foregoing linear alkenyl groups may or may not be substituted with one or more $OR^b$ groups, or may be substituted with an additional carboxylic acid group, or may be substituted with a combination of halogen and $OR^b$ groups or a combination of halogen and additional carboxylic acid groups or a combination of $OR^b$ and additional carboxylic acid groups.

In a fifth set of embodiments, the hydrocarbon group (R) is unsaturated and branched, i.e., a branched olefinic or alkenyl group. Some examples of branched olefinic groups include propen-2-yl ($CH_2$═C.—$CH_3$), 1-buten-2-yl ($CH_2$═C.—$CH_2$—$CH_3$), 1-buten-3-yl ($CH_2$═CH—CH.—$CH_3$), 1-propen-2-methyl-3-yl ($CH_2$═C($CH_3$)—$CH_2$—), 1-penten-4-yl, 1-penten-3-yl, 1-penten-2-yl, 2-penten-2-yl, 2-penten-3-yl, 2-penten-4-yl, and 1,4-pentadien-3-yl, and the numerous other branched alkenyl groups having up to 12 carbon atoms, wherein the dot in any of the foregoing groups indicates a point of attachment. Any of the foregoing branched alkenyl groups may or may not be substituted with one or more halogen (e.g., fluorine, chlorine, bromine, or iodine) atoms to result in partial or complete halogenation of the branched alkenyl group. Any of the foregoing branched alkenyl groups may or may not be substituted with one or more $OR^b$ groups, or may be substituted with an additional carboxylic acid group, or may be substituted with a combination of halogen and $OR^b$ groups or a combination of halogen and additional carboxylic acid groups or a combination of $OR^b$ and additional carboxylic acid groups.

In a sixth set of embodiments, the hydrocarbon group (R) is unsaturated and cyclic, i.e., a cycloalkenyl group. The unsaturated cyclic group can be aromatic or aliphatic. Some examples of unsaturated cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group may or may not also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems. All of the foregoing cyclic groups are carbocyclic groups. Any of the foregoing unsaturated cyclic hydrocarbon groups may or may not be substituted with one or more halogen (e.g., fluorine, chlorine, bromine, or iodine) atoms to result in partial or complete halogenation of the cycloalkenyl group. Any of the foregoing unsaturated cyclic hydrocarbon groups may or may not be substituted with one or more $OR^b$ groups, or may be substituted with an additional carboxylic acid group, or may be substituted with a combination of halogen and $OR^b$ groups or a combination of halogen and additional carboxylic acid groups or a combination of $OR^b$ and additional carboxylic acid groups.

In a seventh set of embodiments, the hydrocarbon group (R) has more than 12 carbon atoms (e.g., at least or more than 15, 20, 25, 30, 35, 40, 45, or 50 carbon atoms) and may even be oligomeric or polymeric. In the case of an oligomeric or polymeric group, the group may be, for example, a polyethylenyl, poly(tetrafluoroethylenyl), or polyethylene glycol group.

In Formula (2), $R^b$ is selected from hydrogen atom and alkyl groups containing one to three carbon atoms. In one set of embodiments, $R^b$ is a hydrogen atom, and R may be any of the linear, branched, or cyclic (and alternatively, saturated or unsaturated) hydrocarbon groups provided above. In another set of embodiments, $R^b$ is an alkyl group, and R may be any of the linear, branched, or cyclic (and alternatively, saturated or unsaturated) hydrocarbon groups provided above.

Some specific examples of carboxylic acids or esters thereof include:

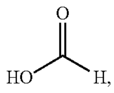, 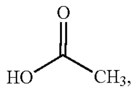, 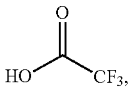, 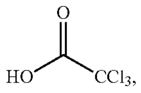, (TFA)

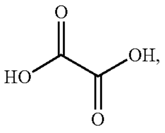, 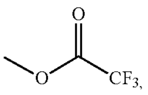, 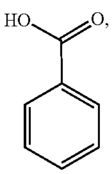, 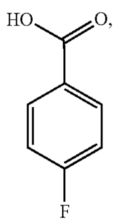,

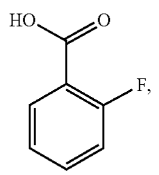, 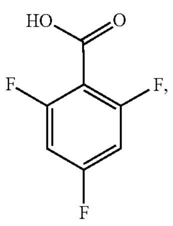, 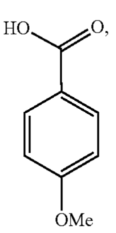,

-continued

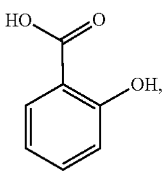
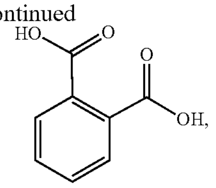
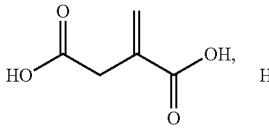
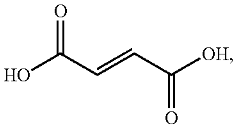
and
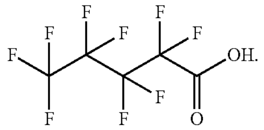

The base may alternatively complex with a sulfonic acid having the general formula $R—SO_3R^b$ (where R and $R^b$ are as defined above and any specific embodiments thereof), such as:

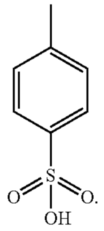

Esters of any of the foregoing acids (i.e., where one or more acidic hydrogen atoms are substituted with one or more $R^b$ alkyl groups) are considered herein.

The catalyst described above can be produced by combining the base and acid components (i.e., according to Formulas (1) and (2), respectively) under conditions where the two components form a complex with each other. Typically, the two components are combined, in the absence or presence of a solvent, and heated to a temperature of 40-80° C. or more particularly 50-70° C., or about 60° C., for a period of time of 15-45 minutes, more typically about 30 minutes.

In another aspect, the present disclosure is directed to methods of deconstructing polymer waste into at least one useful breakdown product by contacting the polymer waste with a catalyst described above under an elevated temperature and in the presence of a protic molecule. For purposes of the present invention, the polymer waste should contain at least one type of condensation polymer, such as a polyester (e.g., PET, PBT, PHT or unsaturated polyester), polyurethane, polycarbonate, and/or polyamide (e.g., a nylon, such as nylon 6, nylon 6,6, or nylon 1,6). In some embodiments, the polymer waste contains at least two or three different types of condensation polymers, such as a polyester and polyurethane, polyester and polycarbonate, polyester and polyamide, polyurethane and polycarbonate, polyurethane and polyamide, or two different types of polyesters, or two different types of polyurethanes, or two different types of polycarbonates, or two different types of polyamides. The polymer waste may also contain different physical forms of the same type of polymer, such as bottles and carpet both made of polyesters, or more specifically, PET. The useful breakdown products typically include monomer species capable of being polymerized. For example, in some embodiments, the polymer waste contains a polyester, such as polyethylene terephthalate (PET), wherein at least one useful breakdown product may be bis(2-hydroxyethyl) terephthalate. An exemplary schematic of the process is shown in FIG. 1B.

As indicated above, the polymer waste is contacted with the catalyst under an elevated temperature and in the presence of a protic molecule. The elevated temperature is effective for inducing catalytic alcoholysis or aminolysis of the condensation polymer. The elevated temperature is typically at least 150° C. and up to 250° C., provided that the temperature is below the decomposition temperature of the polymer waste. In different embodiments, the temperature may be, for example, 150° C., 160° C., 170° C., 180° C., 190° C., 200° C., 210° C., 220° C., 230° C., 240° C., or 250° C., or a temperature within a range bounded by any two of the foregoing values (e.g., 150-250° C., 160-240° C., 170-230° C., 170-220° C., or 170-200° C.). The process may be conducted at any of the foregoing temperatures for a period of time of, for example, 1 hour, 2 hours, 3 hours, or 4 hours, or a period of time within a range therein. The method may be conducted at ambient pressure (about 1 atm) but may, in some embodiments, subject the combined components (polymer waste in contact with catalyst and protic molecule) to an elevated pressure, e.g., above 1 atm, or at least 2, 5, 10, 20, or 50 atm. In some embodiments, the polymer waste includes two or more types of condensation polymer waste, and the two or more types of condensation polymer waste are catalytically deconstructed simultaneously at a single temperature. In other embodiments, the polymer waste includes two or more types of condensation polymer waste, and the two or more types of condensation polymer waste are catalytically deconstructed sequentially at different temperatures.

Some general examples of protic molecules include alcohols, diols, polyols, and amines. Some examples of alcohols include methanol, ethanol, n-propanol, isopropanol, n-butanol, and isobutanol. Some examples of diols include methylene glycol, ethylene glycol, propylene glycol, 1,3-propanediol, poly(ethylene)diol, poly(ethylene glycol), polydimethylsiloxane, and poly(butadiene)diol. Some examples of polyols include glycerol, sugar alcohols (e.g., xylitol and erythritol), and polyether polyols. Some examples of amines include ammonia, methylamine, ethylamine, methylenediamine, ethylenediamine, and ethanolamine. The protic molecule is typically included in at least equal molar amount of the polymer waste. More typically, the protic molecule is included in an excess amount compared to the polymer waste, e.g., at least two times, three times, four times, five times, or ten times the molar amount of polymer waste. The catalyst is typically included in the reaction system in a lower molar amount compared to the molar amount of polymer waste, e.g., no more than 0.25X, 0.2X, 0.1X, or 0.05X, wherein X represents the molar amount of the polymer waste. In some embodiments, after the reaction is complete or near complete, the crude product is mixed with an excess of water to remove excess protic molecule and catalyst from breakdown products.

Examples have been set forth below for the purpose of illustration and to describe certain specific embodiments of the invention. However, the scope of this invention is not to be in any way limited by the examples set forth herein.

EXAMPLES

Overview

Herein is described a highly efficient PIS organocatalyst that can efficiently deconstruct mixed waste of PC, PU, PET, and PA in a single batch via selective cleavage of amide, carbonate, urethane, and ester bonds. FIG. 1 (portion A) includes a schematic of the conventional method while FIG. 1 (portion B) shows possible products produced by the presently disclosed method. The designed organocatalyst can deconstruct condensation polymers selectively, while keeping other polymers including polyolefins (e.g., poly (ethylene) (PE) and poly(propylene) (PP)) or cotton intact, which permits facile separation of non-condensation polymers from the mixture. The described chemical deconstruction process can be applied to the majority of known mixed plastics, and it thus provides a viable step toward the closed-loop circularity of plastics and carbon neutrality.

Methods

Chemicals. All reactions were performed using a heavy wall cylindrical pressure vessel. 1,5,7-triazabicyclo[4.4.0]dec-5-ene (TBD) (98%), trifluoracetic acid (TFA) (99%), ethylene glycol (EG) (99.8%), 7-methyl-1,5,7-triazabicyclo[4.4.0]dec-5-ene (mTBD) (98%), methyl trifluoracetate (mTFA) (99%), dimethyl sulfoxide-d6 (DMSO-d6) (99.9%), and methanol (99%) were used as received without further purification. Polycarbonate (PC, $M_w$=45,000 g/mol) and polyamide (PA, Nylon 6, $M_w$=35,000 g/mol were purchased from a commercial source as granulate and used as received. Poly(ethylene terephthalate) (i.e., PET, $M_w$40,000 g/mol, and 60,000 g/mol) were provided by a commercial source. Polyurethane (PU) was synthesized and characterized by $^1$H NMR. Gel Permeation Chromatography (GPC) determined the molecular weight of PU to be $M_w$24600 g/mol.

Synthetic Procedure. TBD:TFA synthesis: Different dual catalysts were prepared by mixing TBD and TFA at molar ratios of base to acid at 60° C. for 30 or 60 minutes and used without further purification. The following is a general schematic of the process:

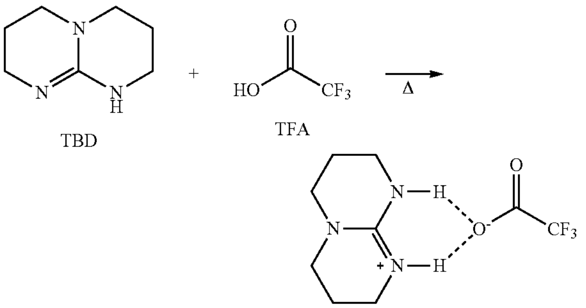
TBD
TFA
TBD:TFA

Different organocatalysts were prepared using different ratios of TBD and TFA, as follows:

| TBD | TFA | TBD:TFA |
|---|---|---|
| 0 | 1 | 0:1 |
| 1 | 0 | 1:0 |
| 1 | 1 | 1:1 |
| 1 | 1.25 | 1:1.2 |
| 1 | 1.5 | 1:1.5 |
| 1 | 1.75 | 1:1.75 |
| 1 | 2 | 1:2 |
| 1 | 3 | 1:3 |
| 1.1 | 1 | 1.1:1 |
| 1.2 | 1 | 1.2:1 |
| 1.3 | 1 | 1.3:1 |
| 1.4 | 1 | 1.4:1 |
| 1.5 | 1 | 1.5:1 |
| 1.75 | 1 | 1.75:1 |
| 2 | 1 | 2:1 |
| 3 | 1 | 3:1 |

Different organocatalysts were prepared using a 1:1 molar ratio of TBD and different acids, as follows:

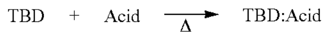

| Acid Name | Acid Structure | OC name |
|---|---|---|
| Formic acid (FA) | 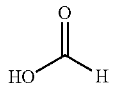 | TBD:FA |
| Acetic acid (AA) | 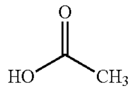 | TBD:AA |
| Trifluoroacetic acid (TFA) | 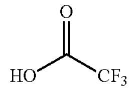 | TBD:TFA |
| Trichloroacetic acid (TCA) | 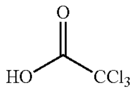 | TBD:TCA |
| Oxalic acid (OA) | 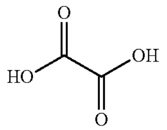 | TBD:OA |
| Methyl-trifluoroacetate (m-TFA) | 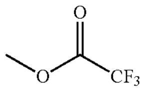 | TBD:mTFA |
| Benzoic acid (BA) | 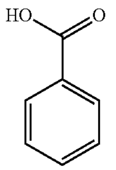 | TBD:BA |
| Flurobenzoic Acid (o-FBA) | 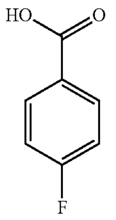 | TBD:p-FBA |

-continued

TBD + Acid $\xrightarrow{\Delta}$ TBD:Acid

| Acid Name | Acid Structure | OC name |
|---|---|---|
| Flurobenzoic Acid (pFBA) | 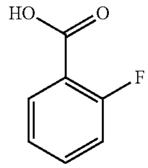 | TBD:o-FBA |
| Trifluorobenzoic Acid (TFBA) | 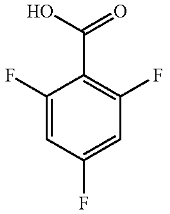 [SMILES: O=C(O)c1c(F)cc(F)cc1F] | TBD:TFBA |
| p-Methoxybenzoic Acid (p-MBA) | 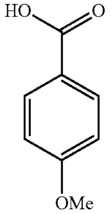 | TBD:p-MBA |
| Salicylic acid (SA) | 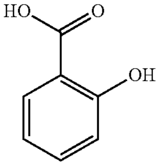 | TBD:SA |
| Phthalic acid (PA) | 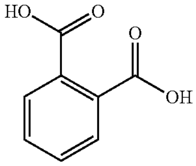 [SMILES: O=C(O)c1ccccc1C(=O)O] | TBD:PA |
| Itaconic acid (IA) | 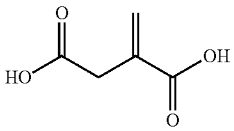 | TBD:IA |
| Maleic acid | 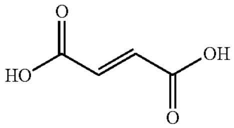 | TBD:MA |
| p-Toluene sulphonic acid (TSA) | 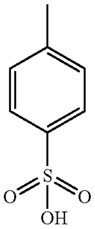 | TBD:TSA |

-continued

TBD + Acid $\xrightarrow{\Delta}$ TBD:Acid

| Acid Name | Acid Structure | OC name |
|---|---|---|
| Perfluoropentanoic acid (PFPA) | 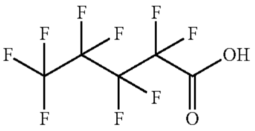 | TBD:TFA |

Different organocatalysts were prepared using a 1:1 molar ratio of different bases, in combination with TFA, as follows:

Base + TFA $\xrightarrow{\Delta}$ Base:TFA

| Base Name | Base Structure | OC name |
|---|---|---|
| Triazabicyclodecane(TBD) | 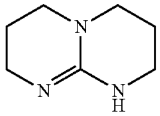 | TBD:TFA |
| Methyl-triazabicyclodecene(mTBD) | 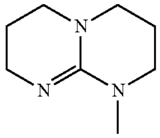 | mTBD:TFA |
| 1,5-Diazabicyclo[4.3.0]non-5-ene(DBN) | 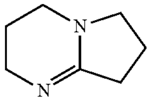 | DBN:TFA |
| 1,8-Diazabicyclo [5.4.0] undec-7-ene (DBU) | 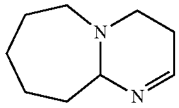 [SMILES: C1=NC2CCCCCN2CC1] | DBU:TFA |
| Trimethylguanidine (TMG) | 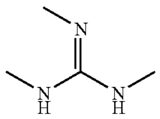 | TMG:TCA |

TBD:TFA (1:1):

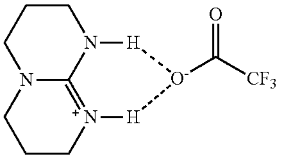

$^{1}H$ NMR (400 MHz, DMSO) δ 8.07 (s, 2H), 3.27 (td, J=6.2, 2.2 Hz, 4H), 3.18 (dq, J=6.0, 2.9 Hz, 4H), 1.88 (dd, J=8.6, 4.0 Hz, 4H). $^{13}C$ NMR (101 MHz, DMSO) δ159.72, 150.83, 118.10, 46.09, 37.33, 20.20.

TBD:TFA (3:1):

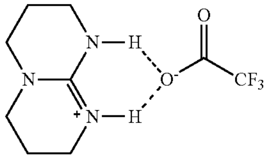

$^1$H NMR (400 MHz, DMSO) δ 5.10 (s, 2H), 3.08 (q, J=5.6 Hz, 8H), 2.02-1.59 (m, 4H).

TBD:TFA (1:3)

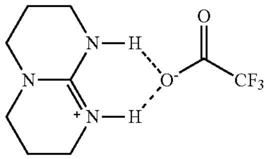

$^1$H NMR (400 MHz, DMSO) δ 15.35 (s, 1H), 7.79 (s, 2H), 3.37-3.21 (m, 4H), 3.17 (s, 4H), 1.85 (s, 4H).

TBD:mTFA (1:1) synthesis:

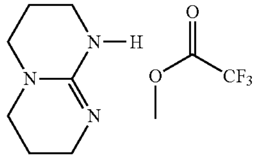

Equimolar amounts of TBD and mTFA were mixed with a magnetic stir bar at 60° C. for 30 minutes and used without further purification. $^1$H NMR (400 MHz, DMSO) δ 3.33-3.13 (m, 8H), 2.90 (s, 3H), 1.89 (ddp, J=16.1, 11.0, 5.9 Hz, 4H).

Synthesis of 1:1 of mTBD:TFA:

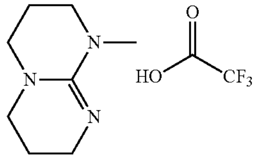

Equimolar amounts of mTBD and TFA were mixed at 60° C. for 30 minutes and used without further purification. $^1$H NMR (400 MHz, DMSO) δ 3.27 (ddt, J=22.1, 10.7, 5.8 Hz, 8H), 2.92 (s, 3H), 1.93 (p, J=6.0 Hz, 2H), 1.86 (p, J=5.9 Hz, 2H).

Poly(urethane) Synthesis:

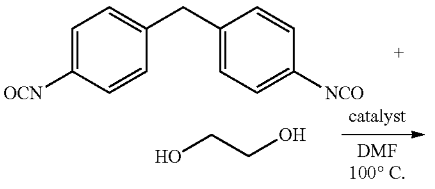

-continued

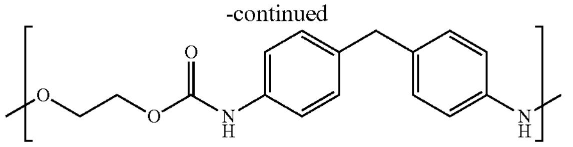

Methylene diphenyl diisocyanate (MDI) (5.3 g, 21.2 mmol), ethylene glycol (1.4 g, 21.2 mmol), dibutyltin dilaurate (5.0 mg), and 50 mL of DMF were put into a 500 mL round-bottom flask, and the reaction was heated at 80° C. in an oil bath. Then, the mixture was left to react for 12 h for complete polymerization. The final viscous solution was poured into 1 L of ethanol. The precipitate was collected and dried in a vacuum oven at 60° C. for 12 h to yield pure polyurethane with $M_w$ 24600 g/mol, PDI 1.23 confirmed by GPC. $^1$H NMR (400 MHz, DMSO) δ 9.64 (s, 2H), 7.35 (d, J=8.1 Hz, 4H), 7.09 (d, J=8.1 Hz, 4H), 4.30 (s, 4H), 3.78 (s, 2H).

PET Polymer Deconstruction

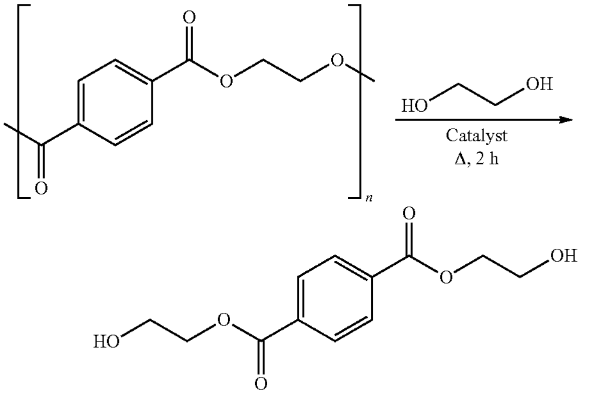

General procedure: PET pellets (0.5 g, 2.60 mmol), EG (1.62 g, 26 mmol), and catalyst (0.035 g, 0.13 mmol) were placed in a pressure vessel with a magnetic stirrer. The deconstruction reactions were conducted at 180° C. for 2 h. When the reaction was completed, the crude product was cooled to room temperature and a large excess of distilled water was added. The resulting solution was vigorously stirred and filtered to separate EG, catalyst, and main product from dimers, oligomers and insoluble in water. The aqueous transparent filtrate was stored in a refrigerator at 4° C. overnight. White needle-like crystals bis(2-hydroxyethyl) terephthalate (BHET) were formed in the solution, which was then recovered by filtration before drying.

BHET: $^1$H NMR (400 MHz, DMSO) δ 8.13 (s, 4H), 4.97 (t, J=5.7 Hz, 2H), 4.36-4.29 (m, 4H), 3.72 (q, J=5.3 Hz, 4H).

BHET Dimer: $^1$H NMR (400 MHz, DMSO) δ 8.15-8.05 (m, 8H), 4.97 (q, J=5.4 Hz, 2H), 4.68 (s, 4H), 4.31 (q, J=4.7 Hz, 4H), 3.71 (p, J=6.4 Hz, 4H).

Catalysis reaction optimization: PET pellets (0.5 g, 2.6 mmol, 1 eq.) were charged in a 10 mL pressure vessel equipped with a magnetic stirrer. Each depolymerization was conducted with 10 equivalents of EG and catalyst at 180° C. temperature for 2 h. The yields were obtained by $^1$H NMR spectroscopy in DMSO-$d_6$ using the catalyst signals as internal standard (d=1.87 ppm, 4H) and the characteristic signals of BHET (d=8.10 ppm, 4H) with corresponding isolated yield.

TABLE 1

| Catalysts Studied for Deconstruction of PET | | | | | |
|---|---|---|---|---|---|
| | | | $C_{PET}$ | % Yield | |
| Entry | Organocatalyst | Ratio | (%) | BHET | Other |
| 1 | TBD:TFA | 1:0 | 60 | 68 | 31 |
| 2 | | 1:1 | 100 | 96 | 2 |
| 3 | | 1:3 | 20 | 50 | 46 |
| 4 | | 3:1 | 100 | 55 | 42 |
| 5 | | 0:1 | 0 | 0 | 0 |
| 7 | mTBD:TFA | 1:1 | 32 | 48 | 46 |
| 8 | TBD:mTFA | 1:1 | 50 | 65 | 34 |

Reaction conditions: PET:Cat:EG (1:0.5:20), yield was calculated by using $^1H$ NMR spectroscopy in DMSO-$d_6$ using the catalyst signals as internal standard (d = 1.87 ppm, 4H), and the characteristic signals of BPA (d = 8.10 ppm, 4H). $C_{PET}$ = Conversion of PET polymer.

TABLE 2

| Reaction Conditions Used for the Deconstruction of PET | | | | |
|---|---|---|---|---|
| | | $C_{PET}$ | Yield (Isolated Yield) | |
| Entry | PET:Catalyst:EG | (%) | BHET | Dimer |
| 1 | 1:0.5:20 | 100 | 93 (90) | 6 |
| 2 | 1:0.5:10 | 100 | 91 (89) | 8 |
| 3 | 1:0.5:5 | 100 | 76 (72) | 18 |
| 4 | 1:0.25:10 | 100 | 91 (89) | 6 |
| 5 | 1:0.1:10 | 100 | 94 (91) | 4 |
| 6 | 1:0.05:10 | 100 | 97 (95) | 1 |

Catalytic activity of PET by using TBD:TFA vs TBD:MSA: In a typical experiment, 1:0.05:10 equivalents of PET pellets, catalyst and EG, respectively, were charged in a 10 mL pressure vessel equipped with a magnetic stirrer. Each deconstruction was carried out at 180° C. for 2 h.

Large scale reaction: PET pellets (10 g, 52 mmol, 1 eq.) were charged into a 150 mL pressure vessel equipped with a magnetic stirrer. The deconstruction was carried out by using 10 eq. of EG and 0.05 eq. of catalyst at 180° C. for 4 h. The yields were calculated using $^1H$ NMR spectroscopy in DMSO-$d_6$ using the catalyst signals as internal standard (d=1.87 ppm, 4H) and the characteristic signals of BHET (d=8.10 ppm, 4H) with corresponding isolated yield.

Catalyst optimization: PET pellets (0.5 g, 2.6 mmol, 1 eq.) were charged into a 10 mL pressure vessel equipped with a magnetic stirrer. Each deconstruction reaction was carried out at a determined EG and catalyst at a certain temperature for 2 h. The yields were calculated using $^1H$ NMR spectroscopy in DMSO-$d_6$ using the catalyst signals as internal standard (d=1.87 ppm, 4H) and the characteristic signals of BHET (d=8.10 ppm, 4H) with corresponding isolated yield.

Polycarbonate (PC) Polymer Deconstruction

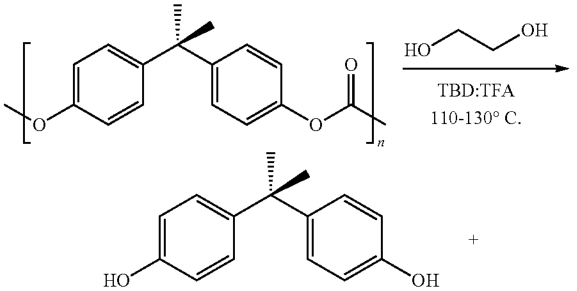

Bisphenol A (BPA)

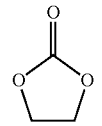

Ethylene carbonate (EC)

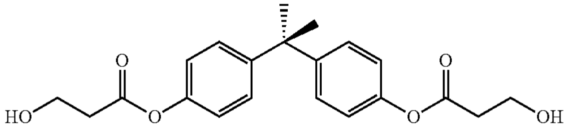

Bis-(Hydroxypropoxy)propane (Bis-HPP)

PC pellets (0.5 g, 1.97 mmol), EG (1.22 g, 19.7 mmol], and catalyst (0.025 g, 0.10 mmol) were placed in a pressure vessel with a magnetic stirrer. The deconstruction was carried out at 130° C. for 2 h. The reaction was then cooled to room temperature before being dissolved in diethyl ether (30 mL) and water (30 mL). Before drying the organic phase with $MgSO_4$, the organic phase was washed three times with water. The mixture was then purified using CombiFlash® to give Bisphenol A (BPA) (94%), ethylene carbonate (93%) and Bis-(hydroxypropoxy) propane (Bis-HPP) (5%). The yield was calculated by using $^1H$ NMR spectroscopy in DMSO-$d_6$ using the catalyst signals as internal standard (d=1.87 ppm, 4H), and the characteristic signals of BPA (δ 6.67 ppm), EC (δ 4.48 ppm), and Bis-HPP (δ 4.08 ppm, 2H). BPA: $^1H$ NMR (400 MHz, DMSO) δ 9.11 (s, 2H), 6.98 (d, J=8.4 Hz, 4H), 6.64 (d, J=8.3 Hz, 4H), 1.53 (s, 6H). EC: $^1H$ NMR (400 MHz, $CDCl_3$) δ 4.48 (s, 4H). Bis-HPP: $^1H$ NMR (400 MHz, $CDCl_3$) δ 7.34-7.25 (m, 4H), 7.22-7.15 (m, 2H), 6.90-6.81 (m, 2H), 4.09 (dd, J=5.2, 3.9 Hz, 4H), 4.01-3.95 (m, 4H), 1.69 (s, 6H).

Polyurethane (PU) Deconstruction

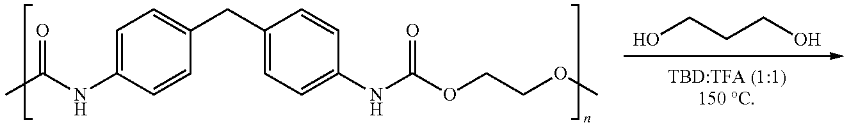

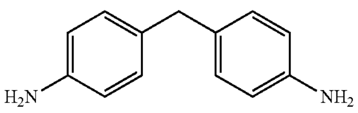

MDA

-continued

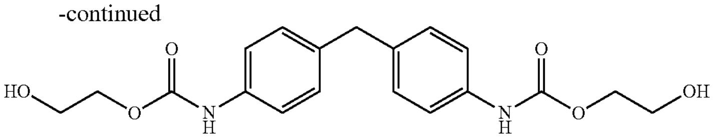

Methylene diethylediamide (MDEA)

PU pellets (0.1 g, 0.32 mmol), EG (0.20 g, 3.20 mmol) and catalyst (0.004 g, 0.016 mmol) were placed in a pressure vessel with a magnetic stirrer. The deconstruction was carried out at 150-170° C. for 2 h. After 2 h, the mixture of 1 M HCl (15 mL) and brine (5 mL) were added. The mixture was extracted with $CH_2Cl_2$ (4× 10 mL), and the combined organic phases were washed with brine (1× 15 mL), dried with anhydrous $Na_2SO_4$, filtered, and dried in vacuo to provide EG as a liquid. The acidic aqueous phase was basified with 4 M NaOH till pH reached 11-12, then extracted with $CH_2Cl_2$ (3× 10 mL). The combined organic phases were dried using anhydrous $Na_2SO_4$, filtered, and dried in vacuo to yield methylene dianiline (MDA) (0.14 g, 80%) and Bis(2-hydroxyethyl) (methylenebis(4,1-phenylene) dicarbamate (BMDC) (<17%). The yield was calculated by $^1$H NMR spectroscopy in DMSO-$d_6$ using the catalyst signals as internal standard (d=1.87 ppm, 4H), and the characteristic signals of MDA (δ 6.8 & 6.5 ppm), and BMDC (δ 7.3 & 7.1 ppm). By increasing temperature, the yield of MDA was increased and BMDC decreased. $^1$H NMR of MDA (400 MHz, DMSO) δ 6.81 (dd, J=7.8, 5.5 Hz, 4H), 6.47 (dd, J=7.8, 5.5 Hz, 4H), 4.82 (br, 4H), 3.59 (s, 2H).

Polyamide (PA) Deconstruction

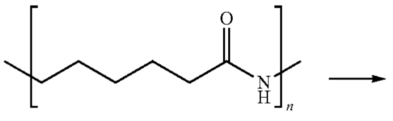

Nylon-6

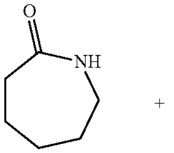

+

Caprolactam (CPL)

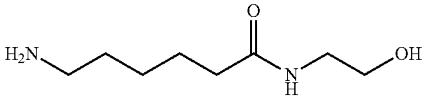

Amino(hydroxyethyl)hexanamide (AHH)

Nylon-6 pellets (0.5 g, 4.4 mmol), EG (2.73 g, 44 mmol), and catalyst (0.05 g, 0.22 mmol) were placed in a pressure vessel with a magnetic stirrer. The deconstruction was carried out at 210° C. for 3 h. After the reaction mixture was cooled down, water was added to it, and then it was separated using CombiFlash®. This made pure caprolactam (CPL) (83%) and 2-hydroxyethyl-6-aminohexanoate (HAH) (13%). The yield was calculated by using $^1$H NMR spectroscopy in DMSO-d6 using the catalyst signals as internal standard (d=1.87 ppm, 4H), and the characteristic signals of BPA (d=2.05 ppm, 4H). $^1$H NMR (400 MHz, DMSO) δ 7.72 (s, 1H), 3.00 (d, J=6.7 Hz, 2H), 2.03 (t, J=7.4 Hz, 2H), 1.63-1.11 (m, 6H).

Selective Deconstruction of Mixed Polymer Pellets

PC pellets (0.33 g, 1.30 mmol), PU pellets (0.41 g, 1.33 mmol), PET pellets (0.25 g, 1.3 mmol), PA pellets (0.15 g, 1.30 mmol), EG (3.17 g, 52 mmol) and TBD:TFA catalyst (0.07 g, 0.26 mmol) were charged into a 30 mL pressure vessel equipped with a magnetic stirrer. In path A, each depolymerization was conducted at a determined temperature (130° C., 160° C., 180° C., and 210° C. for PC, PU, PET, and PA, respectively) for 2 h. At 130° C. only PC is fully deconstructed, whereas the rest of the polymer pellets are unreacted. At 160° C. PU is deconstructed, and PET and PA are still unchanged. Increasing the temperature to 180° C. for another 2 h deconstructs PET. Finally, increasing the temperature to 210° C. deconstructs PA. In path B, deconstruction was carried out at 210° C. and atmospheric pressure for 3 h. The corresponding products (BPA, MDA, BHET, and CPL) were purified by flash column chromatography using different chloroform:methanol mixtures from 1:0 to 1:1 to 0:1 ratios as the eluent. The kinetics, conversion, and yields were determined by 1H NMR spectroscopic analysis of the crude product in DMSO-d6 using the catalyst signals as an internal standard (d=1.87 ppm, 4H). The appearance of the peak at 6.99/6.44/1.53 ppm for BPA, 7.34/7.10 ppm for MDA, 8.17 ppm for BHET, and 2.05 ppm for CPL.

Recyclability and Water Susceptibility

Considering the environmental and economic viability of the proposed process, residual reactants and catalysts need to be recycled for further PET deconstruction. Reusability was studied following two processes, as follows. In the first process (Process-1), after filtering the BHET crystals from the aqueous phase, the unreacted EG and catalyst were dried by vacuum evaporation at 60° C. before being stored in a vacuum oven at 60° C. overnight. Then, fresh PET flakes were added to the recycled system [EG+ catalyst] using the same procedure. In the second process (Process-2), after the complete conversion of the PET, another batch of PET and EG was added without a catalyst to determine the catalytic activity of the catalyst. In the presence of TBD:TFA, the BHET yield is observed to be constant with no loss of catalytic activity, even after five recycling processes. The two methods yielded BHET very efficiently up to 5 cycles. The catalyst also performs very efficiently in the presence of up to 30% of water.

Commercial Polymer Deconstruction

Deconstruction of PC, PU, PET, and PA consumer products: Polymeric consumer product contains additives and is often produced as blends of different polymers. Therefore, the catalyst stability with these complex products was tested in selected experiments. A combination of the plastic (0.5 g) derived from corresponding polymer consumer products, TBD:TFA as catalyst (0.034 g), EG (1.61 g), and temperature (130° C., 160° C., 180° C., and 210° C. for PC, PU, PET and PA consumer product, respectively) for 2 h, were subjected to glycolysis conditions. All tested consumer products were fully deconstructed. The corresponding products (BPA, MDA, BHET and CPL) were purified by either crystallization or flash column chromatography. The conversion and yields were determined by $^1$H NMR spectroscopic analysis of the crude product in DMSO-$d_6$ using the catalyst signals as internal standard (d=1.87 ppm, 4H). The appearance of the peak of the peak at 6.99/6.44/1.53 ppm for BPA, 7.34/7.10 ppm for MDA, 8.17 ppm for BHET and 2.05 ppm for CPL.

Deconstruction of mixed plastic consumer products: In a typical experiment, commercial polymer containing items, such as safety goggles (0.33 g, 1.30 mmol), foam (0.41 g, 1.33 mmol), colored bottles (0.25 g, 1.3 mmol), nylon rope (0.15 g, 1.30 mmol), ethylene glycol (3.17 g, 52 mmol), and TBD:TFA catalyst (0.07 g, 0.26 mmol) were charged into a 30 mL pressure vessel equipped with a magnetic stirrer. In path A, each deconstruction was conducted at a determined temperature (130° C., 160° C., 180° C., and 210° C. for PC, PU, PET, and PA consumer products, respectively) for 2 h. In path B, deconstruction was carried out at 210° C. and atmospheric pressure for 3 h. The corresponding monomers from respective consumer products were purified by flash column chromatography using chloroform:methanol mixture from 1:0 to 1:1 to 0:1 ratio as the eluent. The kinetics, conversion, and yields were determined by $^1$H NMR spectroscopic analysis of the crude product in DMSO-$d_6$ using the catalyst signals as internal standard (d=1.87 ppm, 4H). The appearance of the peak of the peak at 6.99/6.44/1.53 ppm for BPA, 7.34/7.10 ppm for MDA, 8.17 ppm for BHET and 2.05 ppm for CPL.

Selective deconstruction of a mixture of various plastics: The impact of complex polymer mixtures on the catalytic deconstruction reaction was also tested. In the presence of poly(propylene) (PP) cap, and poly(ethylene) (PE) bag, the glycolysis of PET bottle and mixed condensation polymer were conducted using TBD:TFA as catalyst under standard conditions. In these experiments, full conversion of the selected polymer was observed, and none of the described additional polymers hampered the selective deconstruction of the condensation polymer.

Results and Discussion

Figures 2A, 2B:
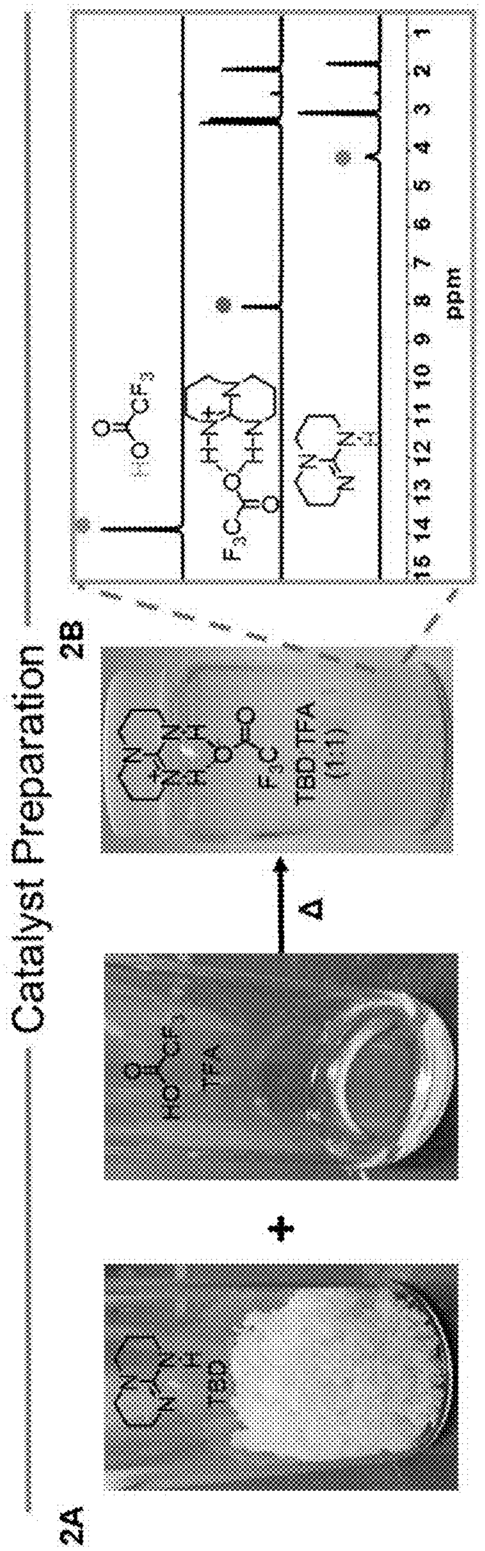
FIGS. 2A-2H. Catalytic activity of the TBD:TFA.
Figures 2C, 2D:
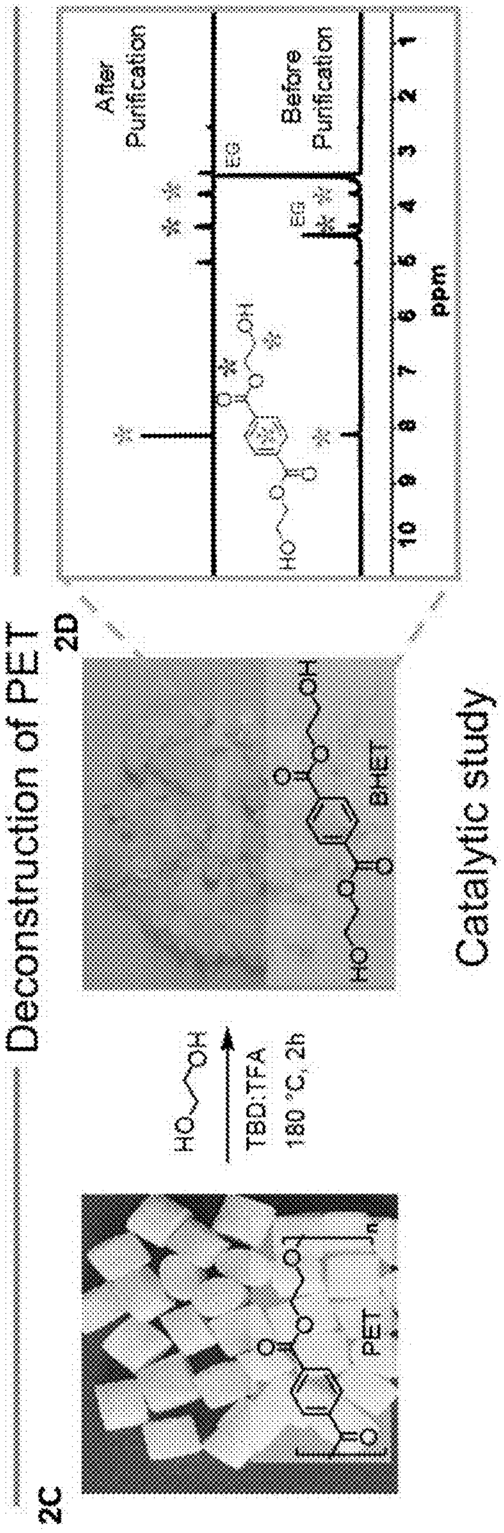

A PIS-based organocatalyst formed from an equimolar amount of TBD and trifluoracetic acid (TFA) was prepared. The resulting catalyst is referred to herein as TBD:TFA. FIG. 2A shows formation of TBD:TFA. The structure of the foregoing catalyst was confirmed by Fourier-transform infrared spectroscopy (FTIR), proton nuclear magnetic resonance ($^1$H NMR) spectroscopy (FIG. 2B), and carbon nuclear magnetic resonance ($^{13}$C NMR) spectroscopy. The $^1$H NMR spectrum (FIG. 2B) shows the disappearance of a peak at δ 13.84 ppm for TFA (FIG. 2B, top) and shifting of the peak from δ 4.14 ppm (FIG. 2B, bottom) for TBD to δ 8.12 ppm, which indicates the formation of the TBD:TFA (FIG. 2B, middle). The design of TBD:TFA stems from the expected coordination ability of protonated TBD ($TBDH^+$) toward the carbonyl (C═O) group and high basicity of TFA anion during glycolysis. The comparatively higher thermal stability of TBD:TFA ($T_{50}$%=215° C.) indicates the formation of thermally stable PIS as compared to those of TBD ($T_{50}$%=175° C.) and TFA ($T_{50}$%=50° C.) individually. Using TBD:TFA as a catalyst, experiments were conducted to investigate the heterogeneous glycolysis of PET ($M_w$40, 000 g/mol) with ethylene glycol (EG) as a reactant and solvent at 180° C. for 2 h (FIG. 2C) to yield bis(2-hydroxyethyl) terephthalate (BHET) (FIGS. 2C and 2D). The PET deconstruction efficiency by the TBD:TFA catalyst was evaluated as a function of EG content (5 to 20 eq.), catalyst amount (0.05 to 0.5 eq), and temperature (150 to 180° C.). PET pellets were deconstructed to yield more than 96% of BHET with a small mixture of oligomer (<4%) at much lower catalyst loading (5 mol %, 0.05 eq.) and less amount of EG (10 eq.) at 180° C. within 2 h, compared to the reported optimized condition of PET glycolysis by TBD: MSA, where ten times catalyst (50 mol %, 0.5 eq.) and twice the amount of EG (20 eq.) are used to yield ~90% BHET monomer (S. R. Nicholson et al., *Annual Review of Chemical and Biomolecular Engineering,* 13(1), 2022).

TBD:TFA and TBD:MSA were compared at the same loading of catalyst (0.05 eq) and EG (10 eq.) for the deconstruction of PET to BHET at 180° C. in 2 h. TBD:TFA showed substantially higher efficiency, exhibiting 100% conversion, while TBD:MSA yielded only about 60% conversion. The same experiment was also performed using TBD:TFA as a catalyst with various molecular weights of PET as well as a larger scale (10 g) of PET, and no significant differences were observed in the efficiency of PET deconstruction.

The catalytic activities of TBD:TFA at different ratios, including TBD:TFA of 1:0, 1:1, 1:3, 3:1, and 0:1, were evaluated to deconstruct PET in the presence of EG at 180° C. Analysis of the final crude products by $^1$H NMR spectroscopy reveals that the reactions with TFA alone or excess TFA deconstruct PET only 0% and 20%, respectively, after 2 h at 180° C. In contrast, the TBD alone and excess TBD (3 eq.) resulted in 60% and 100% conversion, respectively, after 2 h, but yielded a mixture of products (31% and 42%, respectively) besides the BHET monomer, as well as exhibiting low recyclability due to limited thermal stability of the TBD. The highest yield of BHET monomer (>96%) (FIG. 2C and 2D) with a low amount of other oligomer mixture (<4%)) was achieved in a solvent-free reaction and facile crystallization method by using a 1:1 TBD:TFA mixture. Notably, the 1:1 TBD:TFA ratio is also herein referred to as TBD:TFA. The formation of BHET as a major product in the PET deconstruction was further confirmed by $^1$H NMR spectroscopy, Matrix-Assisted Laser Desorption/Ionization-Time Of Flight mass spectrometry (MALDI-TOF MS), and Small-Angle Neutron Scattering (SANS).

Figures 2E, 2F:
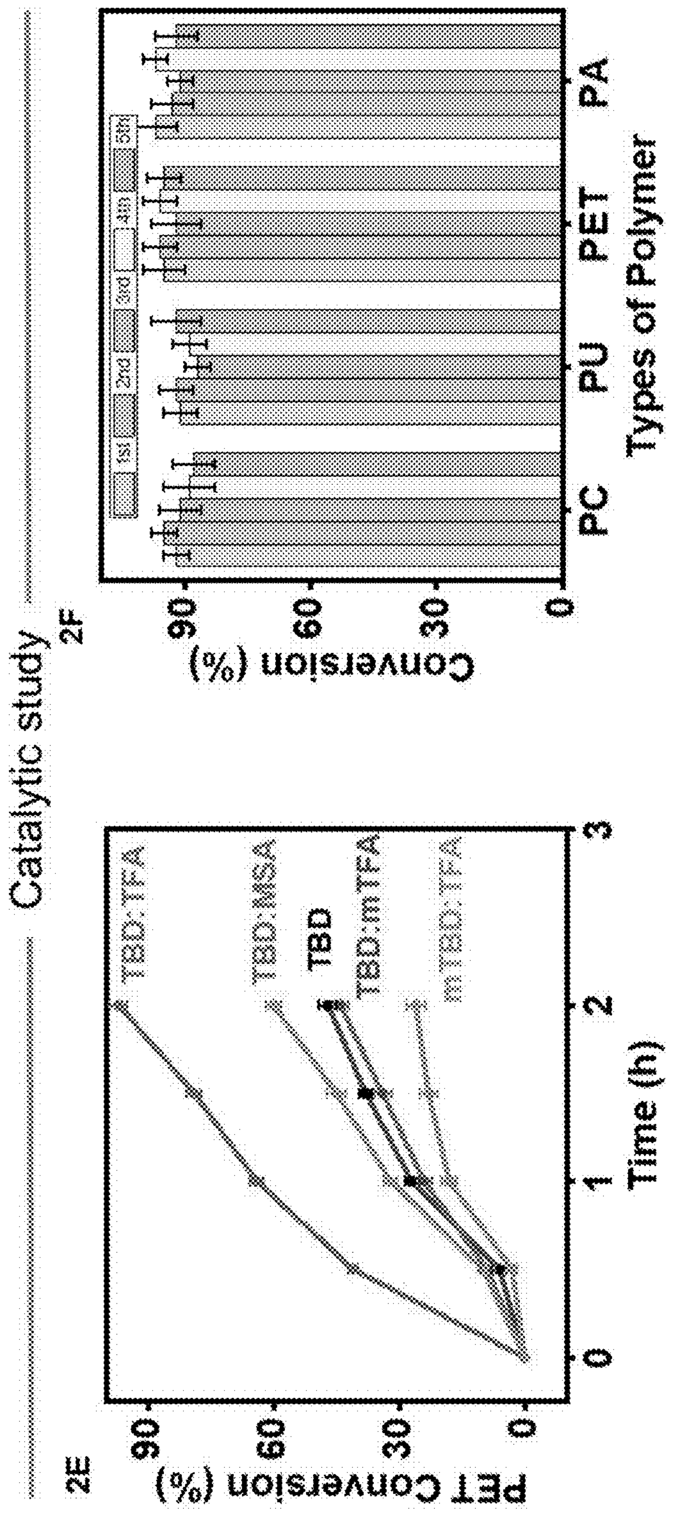
Figure 3:
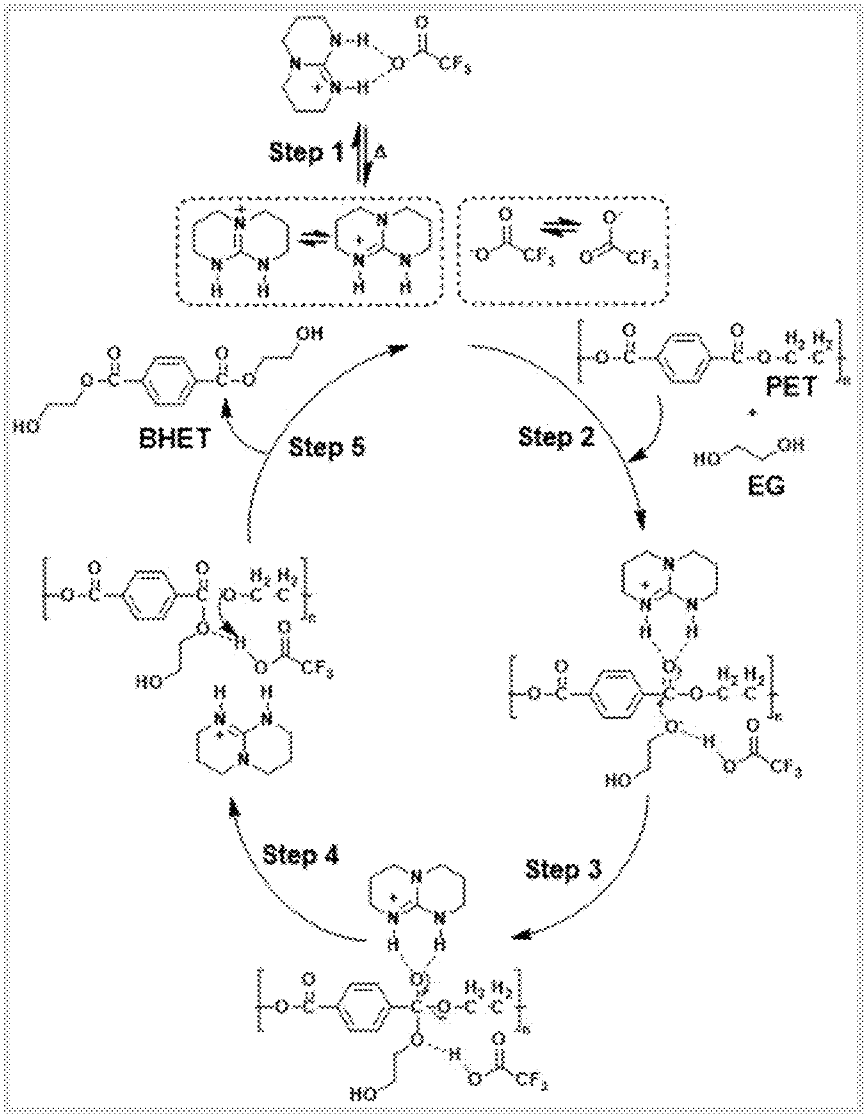
FIG. 3. Scheme showing a proposed deconstruction mechanism of PET with EG using TBD:TFA as a catalyst based on the computational analysis. Step-1: Dual activation mechanism through association and dissociation between TBDH+ and TFA anion for the deconstruction of PET, using EG as a nucleophile, and TBD:TFA as a catalyst, yielding BHET as a product; step-2: Interaction between TBDH+ with PET (ΔE=24.7 kcal/mol) and the TFA anion with EG (ΔE=30.4 kcal/mol); steps 3 & 4: Simultaneous chemical bond formation between PET and EG and proton abstraction by the TFA anion; step-5: Cleavage of the PET to form oligomers and finally monomers.

The catalytic activity of TBD:TFA arises from a dual-activation mechanism by activating both EG and the polymer chain (FIG. 3). The TFA anion activates the nucleophile to be inserted, while $TBDH^+$ activates the polymer chain to be broken by coordinating with the C═O group of the polymer chain (FIG. 3; step 2). To understand the catalytic activity and the mechanism, two more catalysts were synthesized as control. These are referred to as TBD:mTFA and mTBD:TFA, where mTFA and mTBD denote methyl-TFA and methyl-TBD, respectively. Glycolysis of PET using TBD:mTFA and mTBD:TFA exhibits less conversion (50% and 32%, respectively), as well as lower BHET yield (65% and 48%, respectively) due to diminished proton accepting capability by mTBD and absence of a labile proton in mTFA (FIG. 2E).

To further elucidate the highly efficient TBD:TFA catalysis, all-electron density functional theory (DFT) calculations using the hybrid meta functional m06-2x and the aug-cc-pvdz basis set were performed on a model PET chain of eight monomers interacting with $TBDH^+$ and the TFA anion. Notably, the TBD:TFA interaction energy in a continuum solvent model was calculated to be 13.6 kcal/mol (ΔG=3.4 kcal/mol), and ab initio molecular dynamics (MD) shows that TBD:TFA complex can be successfully dissociated into $TBDH^+$ and TFA anions (FIG. 3; step 1) at relatively low temperature. Once dissociated into the cation and anion, DFT results show the formation of a stable complex between $TBDH^+$ and PET with interaction energy of 24.7 kcal/mol.

At the same time, the TFA anion prefers forming a complex with EG at an interaction energy of 30.4 kcal/mol (FIG. 3; step 2). Successive bond formation (FIG. 3; step 3) and bond breaking yield oligomers and finally monomers.

When these DFT results are compared with those of TBD:MSA complex, several notable differences are obtained. First, the interaction energy between TBD and MSA is slightly higher (14.8 kcal/mol). Second, the MSA anion forms a much stronger interaction with PET at 42 kcal/mol than that of TFA at only 13 kcal/mol. Notably, a PET chain, and not just a small molecule model, is required to observe this difference, thus indicating a fundamental role of PET conformations. The overall kinetics between TBD:TFA and TBD:MSA for PET deconstruction rely on (i) the interaction between EG and the anion and (ii) the interaction between $TBDH^+$ and PET through hydrogen-bonding to activate the electrophilicity of the O—C═O bond. The stronger interaction of the MSA anion with PET (42 kcal/mol) appears to hinder the activation of both EG and $TBDH^+$ interaction with O—C═O on PET, thus decreasing the reaction rate. On the other hand, the smaller interaction between the TFA anion and PET (13 kcal/mol) and strong conjugate basicity accelerates the activation of EG and interaction between $TBDH^+$ and O—C═O on PET, thus increasing the overall catalytic activity of TBD:TFA (FIG. 2E).

Figure 2G:
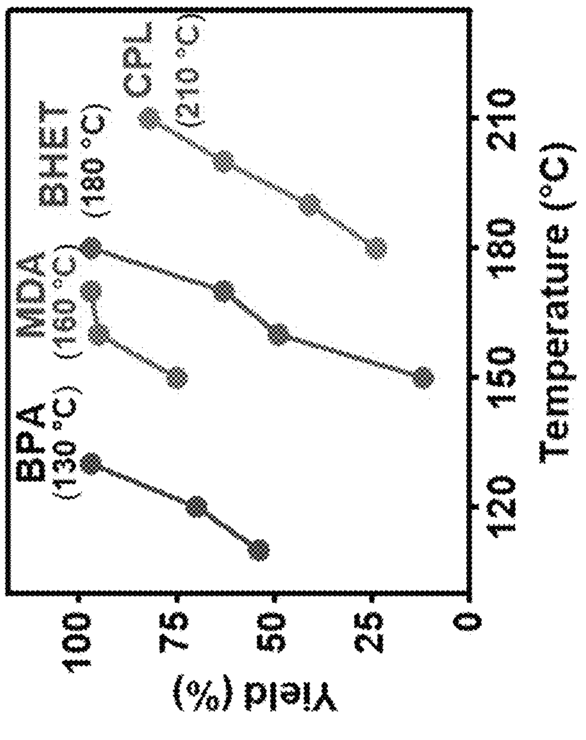
Figure 2H:
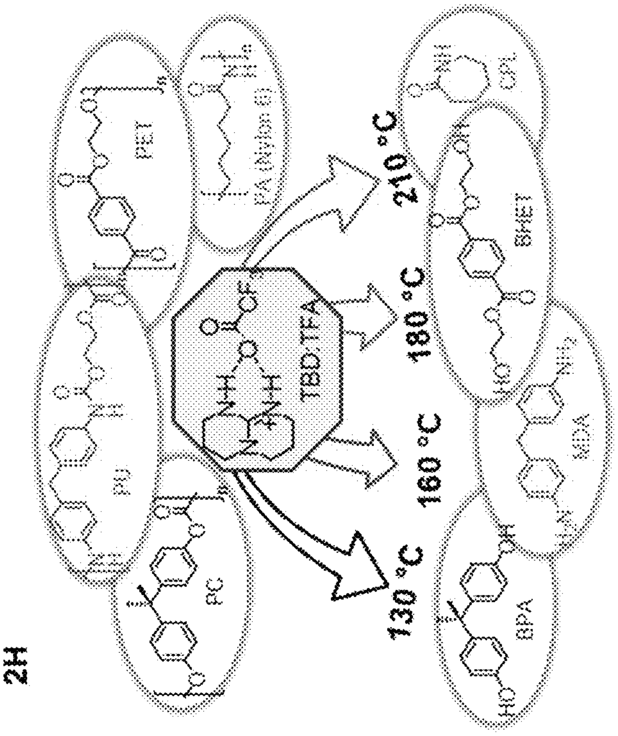

The efficient deconstruction mechanism of PET by TBD:TFA suggests that TBD:TFA can be applied to cleave all types of functional linkages in condensation polymers. The deconstruction of PC (Bisphenol-A based PC, $M_w$ 45,000 g/mol), PU (Diphenylmethylene-ethylene glycol based PU, $M_w$ 24,600 g/mol), PET ($M_w$ 40,000 g/mol) and PA (Nylon 6, $M_w$ 35.000 g/mol) was conducted (FIG. 2G) with the presence of the TBD:TFA catalyst and EG. The structural difference of carbonate, urethane, ester, and amide groups in PC, PU, PET, and PA provides sufficiently different thermodynamics to cause a tailored rate of deconstruction (FIG. 2H). PC, PU, PET, and PA were first deconstructed individually using 10 eq. of EG and 0.05 eq. of TBD:TFA catalyst for 2 h at a specific temperature between 110-210° C. The complete deconstruction within 2 h was demonstrated with >95% yield in PC to bisphenol A (BPA) at 130° C. (FIG. 2H), PU to 4,4'-methylenedianiline (MDA) at 160° C. (FIG. 2H), PET to BHET at 180° C. (FIG. 2H), and PA to caprolactam (CPL) at 210° C. (FIG. 2H). The highly efficient deconstruction of multiple condensation polymers by one kind of catalyst, TBD:TFA, presents a milestone for the chemical recycling of plastics.

Figure 4A:
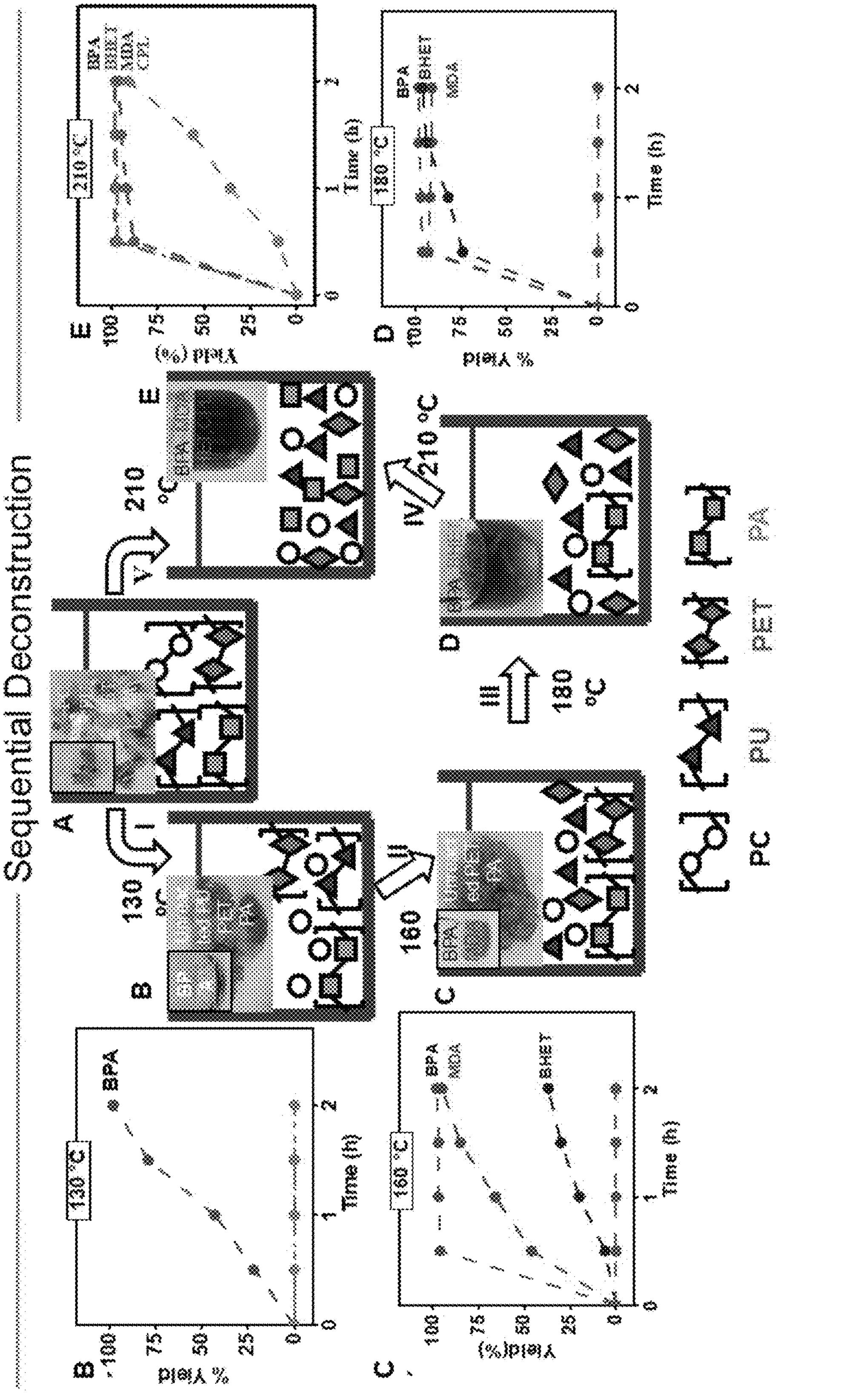
FIGS. 4A-4D. Sequential and selective deconstruction of mixed plastic.

The structural stability among carbonate, urethane, ester, and amide functional groups in PC, PU, PET, and PA, respectively, provides a distinctively different rate of deconstruction that allows selective and sequential deconstruction of mixed PC, PU, PET, and PA with TBD:TFA catalyst. Thus, the concurrent glycolysis of assorted PC, PU, PET, and PA was investigated (FIG. 4A). All polymer pellets (1.3 mmol of each, equivalent to 0.33 g PC, 0.41 g PU, 0.25 g PET, and 0.15 g PA) were mixed in the same vial with EG (10 eq.) and TBD:TFA (0.05 eq.), and the successive deconstruction was monitored at different temperatures. The kinetics by the degree of deconstruction was quantified by $^1H$ NMR spectroscopy using each yielded molecule's characteristic signals (B'-E'). At 130° C., only PC was deconstructed, yielding 97% of BPA after 2 h (B, B'), which demonstrates the capability to selectively deconstruct PC in the co-presence of PU, PET, and PA (B). By increasing the temperature to 160° C., PU is deconstructed to MDA, and a small quantity of PET is also deconstructed to BHET (C, C'). Further elevation of the temperature to 180° C. deconstructs the rest of the PET to yield BHET (D, D'). Finally, at 210° C., PA is deconstructed into CPL (E, E'). Alternatively, directly heating mixed PC, PU, PET, and PA at 210° C. deconstructs all the polymers to yield the mixture of respective monomers, which can be easily separated by fractional distillation or CombiFlash® (V). The ability to deconstruct these mixed condensation polymers provides a clear path to eliminate costly sorting and recover valuable chemicals from mixed plastic wastes.

Figure 4B:
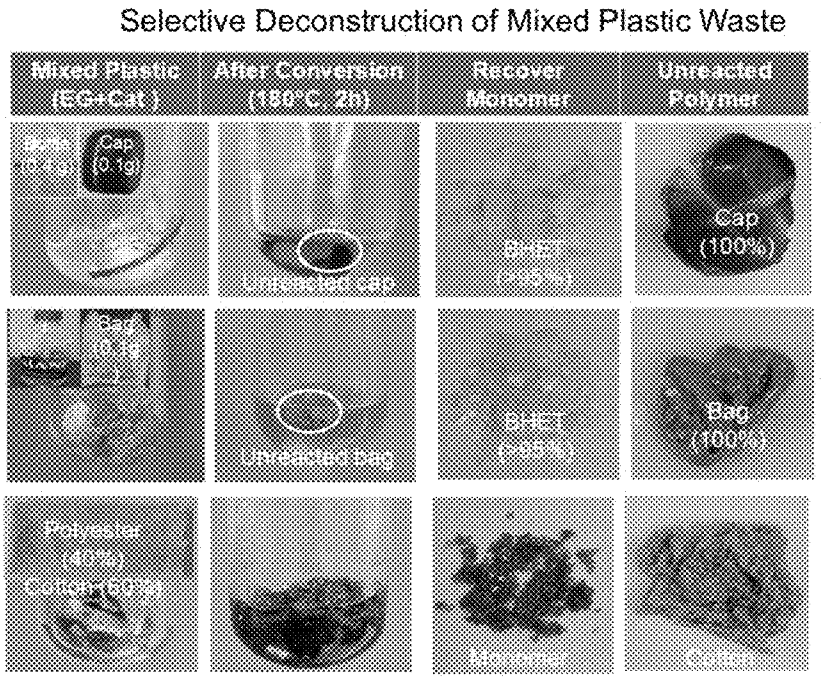
Figures 4C, 4D:
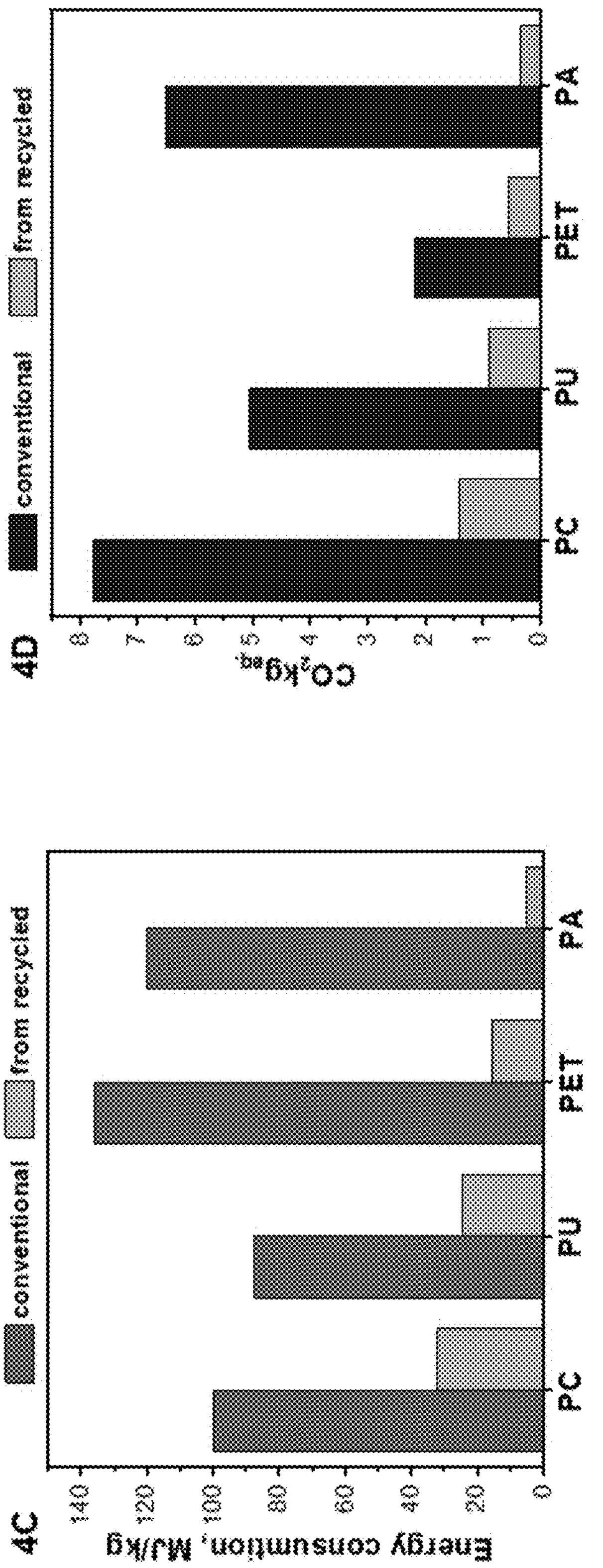

FIG. 4B (top row) shows deconstruction of the PET bottle and PP cap mixture to produce BHET while keeping PP intact. FIG. 4B (middle row) shows that the combination of PC, PU, PET, and PA consumer products with a piece of PE bag is deconstructed to produce corresponding monomer BPA, MDA, BHET, and CPL, respectively, while keeping PE intact. FIG. 4B (bottom row) shows the deconstruction of fabric based on polyester (40%) and cotton (60%) to produce BHET monomer, while unreacted cotton can be readily separated. FIG. 4C shows energy footprint and FIG. 4D shows carbon footprint of PC, PU, PET, and PA production by conventional petroleum-based approach against the reconstruction of PC, PU, PET, and PA using the deconstructed monomer by TBD:TFA-based process.

The sustainability and economic viability of a catalyst depend on its reusability. TBD:TFA was thus evaluated in multi-cycle reuse following two different glycolysis processes. The yield of each catalytic cycle was determined by $^1H$ NMR spectroscopy using a catalyst as the internal standard. For both processes, the catalyst can be used in at least 5 cycles with excellent yield (>90%) for all the examined condensation polymers individually (FIG. 2F). In addition, since water tends to harm the efficiency of organocatalysts, the deconstruction of PET was performed in the presence of water to understand the impact of water on the TBD:TFA catalyst efficiency. The observed result indicates that up to 30% water does not hamper the deconstruction, indicating that the catalyst can deconstruct the plastic waste directly even without drying, thereby saving significant energy and time in its industrial adoption.

The properties of plastics are often tailored to the respective application by blending different additives during their manufacturing, and the mixed state makes the deconstruction of discarded plastics an even greater challenge. Thus, during the present investigation, the efficacy of the TBD:TFA catalyst was further evaluated by deconstructing selected consumer products based on PC, PU, PET, and PA. First, commercially available colorful PET water bottles were cut into small pieces (0.5 g) and deconstructed by loading EG (10 eq.) and TBD:TFA (0.05 eq.) at 180° C. for 2 h. The water bottle was fully converted to BHET. The same deconstruction condition was applied to a polyester-based carpet and cloth, and they exhibited complete conversion. Similarly, a PC-based consumer product, safety goggles, were fully converted to yield pure BPA. PU foam and a nylon rope, as consumer products of PU and PA, were also thoroughly deconstructed to yield the corresponding monomer. These results indicate the broad applicability of TBD:TFA for deconstructing various consumer products and the negligible influence of polymer additives or color pigments on the catalyst activity.

The deconstruction of mixed consumer plastic waste via selective glycolysis was further investigated. A mixture of safety goggles (PC), PU foam, PET water bottle, and nylon rope (PA) (0.5 g each) from customary sources were placed in a reaction vessel, and successive heat was applied by using EG (10 eq.) and TBD:TFA (0.05 eq.) for 2 h to validate the catalyst efficiency in a mixed consumer plastic waste. Reaction temperatures of 130° C. led to the complete conversion of PC waste to BPA, while PU, PET, and PA waste remained unconverted. Because of its insolubility in EG, the unreacted PU, PET, and PA waste can be easily filtered off from the reaction solution and proceed with deconstruction in a subsequent reaction. Increasing the temperature to 160° C. resulted in the complete conversion of PU foam to MDA, and at an elevated temperature of 180° C., the PET water bottle is fully converted to BHET. The nylon rope is intact after 160° C. or 180° C. deconstruction conditions; thus, it can be easily separated. When the residue is heated to 210° C., the nylon rope is fully deconstructed to CPL. In another way, TBD:TFA catalyst was used to deconstruct mixed plastic wastes of the same consumer products in the same reactor at 210° C. for 2 h, yielding a mixture of BPA, MDA, BHET, and CPL, which was subsequently separated by fractional distillation or CombiFlash®.

The organocatalyst TBD:TFA can deconstruct specific plastics (PC, PU, PET, and PA) and leave other plastics intact through their reactivity differences in the polymer structure, solvation, as well as physical and mass transport properties. To evaluate the efficiency and selectivity of TBD:TFA as a catalyst for multiple mixed wastes, TBD:TFA-based glycolysis was performed by using (i) a PET bottle with a PP cap (FIG. 4F), (ii) a PET bottle with PE bags, (iii) a mixture of PC, PU, PET and PA based consumer products with PE bags (FIG. 4G), and (iv) fabrics consisting of 40% polyester and 60% cotton (FIG. 4H). Due to the presence of labile linkage (O—C═O, ester or —N—C═O, amide), condensation polymers exhibit complete conversion to yield respective monomer while keeping unreacted PP (100%), PE (100%), and cotton (100%). This selective deconstruction method using TBD:TFA will eliminate the need for upfront separation of mixed plastics and can also apply to multicomponent plastics, such as multi-layer packaging or textiles.

Evaluating energy and carbon inputs are critical for understanding their circular plastic and environmental impacts. Commonly, the production of virgin polymers involves a long list of processes, from raw material extraction to waste management process, which has a considerable impact on embodied carbon and energy demand in the final plastic product ranging from 1.9 to 5.8 kg $CO_2$ eq./$kg_{polymer}$ and 51 to 176 MJ/kg, respectively (S. R. Nicholson et al., Ibid.). Recycling polymer waste and reconstructing new polymeric materials have decreased the impact on embodied carbon by a factor of 6-10 in some cases (P. A. Wager et al., *Science of the Total Environment* 2015, 529, 158-167). Life Cycle Assessment (LCA) modeling is an integral tool to evaluate the environmental impact of the developed approach in deconstruction of each polymer individually and the production of reconstructed polymers from the recycled monomer.

A cradle-to-gate LCA study was herein performed to estimate the carbon and energy footprint in the chemical recycling of PC, PET, PU, and PA waste, followed by the production of PC, PET, PU, and PA. The analysis considers any options that influence the environment by consuming resources or releasing emissions, including resource use, human health, and ecological impacts. EG and electricity are the main contributors to the environmental impacts of the polymer deconstruction process by mainly affecting ozone depletion, global warming, and acidification. Due to the efficient deconstruction process of each condensation polymer with TBD:TFA catalyst, the resulting deconstructed monomers produce the corresponding polymers with low embodied carbon values (0.34-1.41 kg $CO_2$ eq.) and cumulative energy demand (4.96-32.0 MJ/kg). The comparative LCA analysis shows that the synthesis of PC, PU, PET, and PA from the deconstructed monomers results in 82%, 81%, 75%, and 95% less GHG emissions (FIG. 4I), as well as 68%, 72%, 84%, and 94% less energy (FIG. 4J) input than that from the traditional petroleum-based monomers, respectively. Moreover, the comparative LCA model for mixed plastic waste of PC, PU, PET, and PA shows a reduction of 51% of fossil energy consumption compared to the combined energy demand for each polymer individually. The significant decrease in carbon and energy footprints in the reconstructed polymers using the deconstructed monomers from TBD:TFA-based process is attributed to the combination of several factors, including the effectiveness of the catalyst, the ability to recycle the excess of EG, fast kinetics, and high yields of polymer deconstruction. Furthermore, simultaneous recovery of intact plastics, such as polyolefins and cellulose (FIGS. 4F, 4G, and 4H), is expected to further reduce GHG and energy input for the overall circularity of multiple plastics.

In summary, the chemical recycling of condensation polymers, PC, PET, PU, and PA and their various mixed plastics was herein demonstrated to address the global challenge of plastic recycling. Using the process disclosed herein, a wide range of post-consumer plastic waste, such as bottles, packaging, foam, carpet, etc. can be readily deconstructed into monomers with high efficiency. The process is also straightforward, solvent-free, low-energy, and greener than conventional processes. The present approach using a TBD:TFA organocatalyst permits efficient and versatile conversion of plastic wastes to high-value chemicals that can be readily used to reproduce high-value plastics or other valuable materials. The tailored catalyst design allows for 100% conversion of polymers to monomer within 2 h using 1/10 of the catalyst and half of EG compared to the state-of-the-art organocatalyst. Furthermore, the reagent and the catalyst are easily recyclable, demonstrating the same catalytic activity even after five repeated reactions with reuse of the same catalyst. Moreover, the developed organocatalyst accomplished the deconstruction of various consumer plastic mixtures, which permits the selective glycolysis of condensation polymers and a facile separation path for the other intact polymers. The approach offers a highly efficient closed-loop chemical upcycling of mixed plastics by facile deconstruction and separation, leading to a more than 80% reduction in energy and carbon footprint.

While there have been shown and described what are at present considered the preferred embodiments of the invention, those skilled in the art may make various changes and modifications which remain within the scope of the invention defined by the appended claims.

What is claimed is:

1. A method of deconstructing polymer waste into at least one useful breakdown product, wherein the polymer waste contains at least one condensation polymer selected from the group consisting of polyester, polyurethane, polycarbonate, and polyamide types, the method comprising contacting the polymer waste with a catalyst comprising an organic nitrogen-containing base and trifluoroacetic acid or ester thereof, in the presence of a protic molecule selected from alcohols, diols, polyols, and amines, at an elevated temperature effective for inducing alcoholysis or aminolysis of the condensation polymer, wherein the useful breakdown products comprise monomer species capable of being polymerized, and the organic nitrogen-containing base has the following structure:

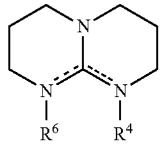

(1f)

wherein:

$R^4$ and $R^6$ are independently selected from hydrogen atom, electron pair, and alkyl groups containing one to three carbon atoms; and the dotted lines represent optional double bonds.

2. The method of claim 1, wherein the protic molecule is a diol.

3. The method of claim 2, wherein the diol is ethylene glycol.

4. The method of claim 1, wherein the polymer waste contains at least two different types of condensation polymers selected from the group consisting of polyester, polyurethane, polycarbonate, and polyamide types.

5. The method of claim 1, wherein the polymer waste contains a polyester.

6. The method of claim 5, wherein the polyester is polyethylene terephthalate.

7. The method of claim 6, wherein at least one useful breakdown product is bis(2-hydroxyethyl) terephthalate.

8. The method of claim 1, wherein the organic nitrogen-containing base (B) and carboxylic acid or ester thereof (A) are present in a B: A molar ratio within a range of 0.05:1 to 1:0.05.

9. The method of claim 1, wherein the organic nitrogen-containing base (B) and carboxylic acid or ester thereof (A) are present in a B: A molar ratio within a range of 0.2:1 to 1:0.2.

10. The method of claim 1, wherein the organic nitrogen-containing base (B) and carboxylic acid or ester thereof (A) are present in a B: A molar ratio within a range of 0.5:1 to 1:0.5.

11. The method of claim 1, wherein the organic nitrogen-containing base (B) and carboxylic acid or ester thereof (A) are present in a B: A molar ratio of about 1:1.

12. The method of claim 1, wherein the polymer waste contains at least three different types of condensation polymers selected from the group consisting of polyester, polyurethane, polycarbonate, and polyamide types.

13. The method of claim 1, wherein the polymer waste contains polyester, polyurethane, polycarbonate, and polyamide types of condensation polymers.

* * * * *